(12) United States Patent
Turner et al.

(10) Patent No.: US 8,242,102 B2
(45) Date of Patent: Aug. 14, 2012

(54) QUINOLINE COMPOUNDS SUITABLE FOR TREATING DISORDERS THAT RESPOND TO MODULATION OF THE SEROTONIN 5-HT6 RECEPTOR

(75) Inventors: Sean Colm Turner, Ludwigshafen (DE); Andreas Haupt, Ludwigshafen (DE); Wilfried Braje, Ludwigshafen (DE); Udo Lange, Ludwigshafen (DE); Karla Drescher, Ludwigshafen (DE); Karsten Wicke, Ludwigshafen (DE); Liliane Unger, Ludwigshafen (DE); Mario Mezler, Ludwigshafen (DE); Wolfgang Wernet, Neustadt (DE); Alfred Hahn, legal representative, Mannheim (DE); Matthias Mayrer, Ludwigshafen (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 156 days.

(21) Appl. No.: 12/532,407

(22) PCT Filed: Mar. 23, 2008

(86) PCT No.: PCT/EP2008/053387
§ 371 (c)(1), (2), (4) Date: Feb. 2, 2010

(87) PCT Pub. No.: WO2008/116831
PCT Pub. Date: Oct. 2, 2008

(65) Prior Publication Data
US 2011/0009380 A1  Jan. 13, 2011

(30) Foreign Application Priority Data
Mar. 23, 2007  (EP) ..................... 07104806

(51) Int. Cl.
A61K 31/397  (2006.01)
C07D 215/00  (2006.01)
(52) U.S. Cl. ............. 514/210.2; 514/312; 546/153
(58) Field of Classification Search ........ 514/210.2, 514/312; 546/153
See application file for complete search history.

(56) References Cited

U.S. PATENT DOCUMENTS

| | | | |
|---|---|---|---|
| 6,586,420 B1 * | 7/2003 | Yazaki et al. | 514/210.21 |
| 7,799,782 B2 * | 9/2010 | Munson et al. | 514/234.5 |
| 2005/0153421 A1 | 7/2005 | Murao et al. | |
| 2007/0027161 A1 | 2/2007 | Harris et al. | |
| 2009/0012056 A1 * | 1/2009 | Ahmed et al. | 514/210.21 |

FOREIGN PATENT DOCUMENTS

| | | |
|---|---|---|
| WO | 03/080680 A | 10/2003 |
| WO | 03080580 | 10/2003 |
| WO | 03080680 | 10/2003 |
| WO | 03082286 | 10/2003 |
| WO | 03104193 | 12/2003 |
| WO | 2004099214 | 11/2004 |
| WO | 2005026125 | 3/2005 |
| WO | 2005/113539 A | 12/2005 |
| WO | 2005113539 | 12/2005 |
| WO | 2007/039219 A | 4/2007 |
| WO | 2007039219 | 4/2007 |
| WO | 2008113818 | 9/2008 |

OTHER PUBLICATIONS

Wesolowska, A., "In the Search for Selective Ligands of 5-HT5, 5-HT6, and 5-HT7 Serotonin Receptors," Pol. J. Pharmacol, 2002, 54, pp. 327-341.
Romero, G., et al., "Efficacy of Selective 5-HT6 Receptor Ligands Determined by Monitoring 5-HT6 Receptor-mediated cAMP signaling Pathways," British Journal of Pharmacology (2006), 148, pp. 1133-1143.

* cited by examiner

*Primary Examiner* — Rei-tsang Shiao
(74) *Attorney, Agent, or Firm* — Lisa V. Mueller; Michael Best & Friedrich LLP

(57) ABSTRACT

The present invention relates to novel quinoline compounds. The compounds possess valuable therapeutic properties and are particularly suitable, for treating diseases that respond to modulation of the serotonin 5-HT$_6$ receptor.

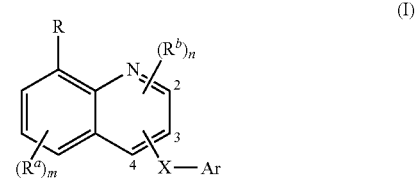

(I)

wherein
R is a moiety of the formula

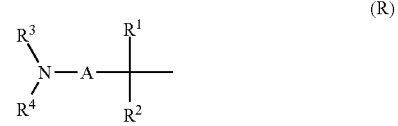

(R)

wherein A, $R^1$ to $R^4$ are as defined in the claims and the specification,
n is 0, 1 or 2;
m is 0, 1, 2 or 3;
$R^a$, $R^b$ are independently selected from the group consisting of halogen, CN, $C_1$-$C_4$-alkyl, $C_1$-$C_4$-haloalkyl, $C_1$-$C_4$-alkoxy, $C_1$-$C_4$-haloalkoxy, $C(O)R^{aa}$, $C(O)NR^{cc}R^{bb}$ and $NR^{cc}R^{bb}$;
X is $CH_2$, $C(O)$, S, $S(O)$ or $S(O)_2$; which is located in the 3- or 4-position of the quinoline ring;
Ar is a radical $Ar^1$, $Ar^2$—$Ar^3$ or $Ar^2$—O—$Ar^3$, wherein $Ar^1$, $Ar^2$ and $Ar^3$ are each independently selected from the group consisting of aryl or hetaryl wherein aryl or hetaryl moieties may be unsubstituted or may carry 1, 2, 3 substituents $R^x$, wherein
and physiologically tolerated acid addition salts and the N-oxides thereof.

23 Claims, No Drawings

QUINOLINE COMPOUNDS SUITABLE FOR TREATING DISORDERS THAT RESPOND TO MODULATION OF THE SEROTONIN 5-HT6 RECEPTOR

RELATED APPLICATION INFORMATION

This application is filed under 35 USC §371 from and claims priority to PCT Patent Application No. PCT/EP2008/053387, which claims the priority benefit of European application serial number EP 07104806.0, filed on Mar. 23, 2007, the teachings and content of which are hereby incorporated by reference herein.

BACKGROUND OF THE INVENTION

The present invention relates to novel quinoline compounds. The compounds possess valuable therapeutic properties and are particularly suitable, for treating diseases that respond to modulation of the serotonin 5-HT$_6$ receptor.

Serotonin (5-hydroxytryptamine, 5-HT), a monoamine neurotransmitter and local hormone, is formed by the hydroxylation and decarboxylation of tryptophan. The greatest concentration is found in the enterochromaffin cells of the gastrointestinal tract, the remainder being predominantly present in platelets and in the Central Nervous System (CNS). 5-HT is implicated in a vast array of physiological and pathophysiological pathways. In the periphery, it contracts a number of smooth muscles and induces endothelium-dependent vasodilation. In the CNS, it is believed to be involved in a wide range of functions, including the control of appetite, mood, anxiety, hallucinations, sleep, vomiting and pain perception.

Neurons that secrete 5-HT are termed serotonergic. The function of 5-HT is exerted upon its interaction with specific (serotonergic) neurons. Until now, seven types of 5-HT receptors have been identified: 5-HT$_1$ (with subtypes 5-HT$_{1A}$, 5-HT$_{1B}$, 5-HT$_{1D}$, 5-HT$_{1E}$ and 5-HT$_{1F}$), 5-HT$_2$ (with subtypes 5-HT$_{2A}$, 5-HT$_{2B}$ and 5-HT$_{2C}$), 5-HT$_3$, 5-HT$_4$, 5-HT$_5$ (with subtypes 5-HT$_{5A}$ and 5-HT$_{5B}$), 5-HT$_6$ and 5-HT$_7$. Most of these receptors are coupled to G-proteins that affect the activities of either adenylate cyclase or phospholipase Cγ.

The human 5-HT$_6$ receptors are positively coupled to adenylyl cyclase. They are distributed throughout the limbic, striatal and cortical regions of the brain and show a high affinity to antipsychotics.

The modulation of the 5-HT$_6$ receptor by suitable substances is expected to improve certain disorders including cognitive dysfunctions, such as a deficit in memory, cognition and learning, in particular associated with Alzheimer's disease, age-related cognitive decline and mild cognitive impairment, attention deficit disorder/hyperactivity syndrome, personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowl Syndrome, diseases associated with neurodegeneration, such as stroke, spinal or head trauma and head injuries, such as hydrocephalus, drug addiction and obesity.

Quinoline compounds having an affinity for the 5-HT$_6$ receptor have been described in the prior art, e.g. in US 2007/0027161, WO 05/026125 and WO 03/080580. The compounds disclosed therein carry a piperazin-1-yl radical in the 8-position of the quinoline moiety. The compounds are mentioned to be useful for the treatment of 5-HT$_6$ receptor-related disorders.

WO 05/113539 describes quinoline compounds which carry a N-bound heterocyclic radical in the 8-position having an affinity for the 5-HT$_6$ receptor.

The intermediately published WO 07/039,219 describes quinoline compounds of formula (1),

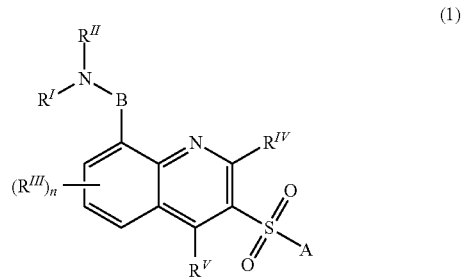

wherein B is —(CH$_2$)$_m$— or —(CR$^{IIX}$R$^{IX}$)—, with m being 2 to 4 and R$^{IIX}$ and R$^{IX}$ being H or C$_1$-C$_3$-alkyl having an affinity for the 5-HT$_6$ receptor.

However, there is still an ongoing need for providing compounds having high affinity for the 5-HT$_6$ receptor and which show high selectivity to this receptor. In particular the compounds should have low affinity to adrenergic receptors, such as $_1$-adrenergic receptor, histamine receptors, such as H$_1$-receptor, and dopaminergic receptors, such as D$_2$-receptor, in order to avoid or reduce considerable side effects associated with modulation of these receptors, such as postural hypotension, reflex tachycardia, potentiation of the antihypertensive effect of prazosin, terazosin, doxazosin and labetalol or dizziness associated to the blockade of the $_1$-adrenergic receptor, weight gain, sedation, drowsiness or potentiation of central depressant drugs associated to the blockade of the H$_1$-receptor, or extrapyramidal movement disorder, such as dystonia, parkinsonism, akathisia, tardive dyskinesia or rabbit syndrome, or endocrine effects, such as prolactin elevation (galactorrhea, gynecomastia, menstruyl changes, sexual dysfunction in males), associated to the blockade of the D$_2$-receptor.

It is an object of the present invention to provide compounds which have a high affinity and selectivity for the 5-HT$_6$ receptor, thus allowing the treatment of disorders related to or affected by the 5-HT$_6$ receptor.

The compounds should also have good pharmacological profile, e.g. a good brain plasma ratio, a good bioavailability, good metabolic stability, or a decreased inhibition of the mitochondrial respiration.

SUMMARY OF THE INVENTION

It has now been found that the quinoline compounds of the formula (I) as defined herein, their physiologically tolerated acid addition salts and the N-oxides thereof exhibit to a surprising and unexpected degree, selective binding to the 5-HT$_6$ receptor. Therefore, the present invention relates to the compounds of formula (I)

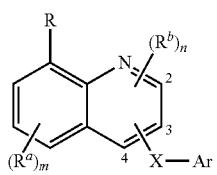

(I)

wherein
R is a moiety of the formula

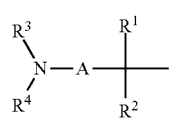

(R)

wherein
A is a chemical bond, $CHR^5$ or $CH_2CHR^5$;
$R^1$ is hydrogen, $C_1$-$C_4$-alkyl, $C_1$-$C_4$-haloalkyl, $C_1$-$C_4$-alkoxy or $C_1$-$C_4$-haloalkoxy;
$R^2$ is hydrogen, $C_1$-$C_4$-alkyl, $C_1$-$C_4$-haloalkyl, $C_1$-$C_4$-alkoxy or $C_1$-$C_4$-haloalkoxy;
$R^3$ is hydrogen or $C_1$-$C_4$-alkyl;
$R^1$ and $R^3$ together may also be linear $C_1$-$C_4$-alkylene, which may carry 1 or 2 radicals $R^6$;
$R^4$ is hydrogen, $C_1$-$C_6$-alkyl, $C_1$-$C_6$-hydroxyalkyl, $C_1$-$C_6$-haloalkyl, $C_1$-$C_6$-alkoxy-$C_1$-$C_4$-alkyl, $C_1$-$C_6$-haloalkoxy-$C_1$-$C_4$-alkyl, $C_3$-$C_6$-cycloalkyl, $C_3$-$C_6$-halocycloalkyl, $C_3$-$C_6$-cycloalkyl-$C_1$-$C_4$-alkyl, aryl-$C_1$-$C_4$-alkyl, hetaryl-$C_1$-$C_4$-alkyl, $C_3$-$C_6$-alkenyl, $C_3$-$C_6$-haloalkenyl, formyl, $C_1$-$C_4$-alkylcarbonyl or $C_1$-$C_4$-alkoxycarbonyl;
$R^5$ is hydrogen, $C_1$-$C_4$-alkyl, $C_1$-$C_4$-haloalkyl, $C_1$-$C_4$-alkoxy or $C_1$-$C_4$-haloalkoxy;
$R^1$ and $R^5$ together may also be a single bond or linear $C_1$-$C_4$-alkylene, which may carry 1 or 2 radicals $R^7$; or
$R^3$ and $R^5$ together may also be linear $C_1$-$C_4$-alkylene, which may carry 1 or 2 radicals $R^8$;
$R^6$ is $C_1$-$C_4$-alkyl, $C_1$-$C_4$-haloalkyl, $C_1$-$C_4$-alkoxy or $C_1$-$C_4$-haloalkoxy; or
$R^5$ and $R^6$ together may also be linear $C_1$-$C_4$-alkylene, which may carry 1 or 2 radicals $R^9$;
$R^7$, $R^8$ and $R^9$ are independently selected from the group consisting of $C_1$-$C_4$-alkyl, $C_1$-$C_4$-haloalkyl, $C_1$-$C_4$-alkoxy and $C_1$-$C_4$-haloalkoxy;
n is 0, 1 or 2;
m is 0, 1, 2 or 3;
$R^a$, $R^b$ are independently selected from the group consisting of halogen, CN, $C_1$-$C_4$-alkyl, $C_1$-$C_4$-haloalkyl, $C_1$-$C_4$-alkoxy, $C_1$-$C_4$-haloalkoxy, $C(O)R^{aa}$, $C(O)NR^{cc}R^{bb}$ and $NR^{cc}R^{bb}$;
wherein $R^{aa}$ is hydrogen, $C_1$-$C_4$-alkyl, $C_1$-$C_4$-haloalkyl, $C_1$-$C_4$-alkoxy or $C_1$-$C_4$-haloalkoxy, and
$R^{cc}$, $R^{bb}$ are independently selected from the group consisting of hydrogen and $C_1$-$C_4$-alkyl;
X is $CH_2$, $C(O)$, S, $S(O)$ or $S(O)_2$; which is located in the 3- or 4-position of the quinoline ring;
Ar is a radical $Ar^1$, $Ar^2$—$Ar^3$ or $Ar^2$—O—$Ar^3$, wherein $Ar^1$, $Ar^2$ and $Ar^3$ are each independently selected from the group consisting of aryl or hetaryl wherein aryl or hetaryl moieties may be unsubstituted or may carry 1, 2, 3 substituents $R^x$, wherein $R^x$ is halogen, CN, $NO_2$, $C_1$-$C_6$-alkyl, $C_1$-$C_6$-haloalkyl, $C_1$-$C_6$-hydroxyalkyl, $C_1$-$C_6$-alkoxy-$C_1$-$C_4$-alkyl, $C_2$-$C_6$-alkenyl, $C_2$-$C_6$-haloalkenyl, $C_3$-$C_6$-cycloalkyl, $C_3$-$C_6$-halocycloalkyl, $C_1$-$C_6$-alkoxy, $C_1$-$C_6$-hydroxyalkoxy,
$C_1$-$C_6$-alkoxy-$C_1$-$C_4$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_6$-alkylcarbonyl, $C_1$-$C_6$-haloalkylcarbonyl, $C_1$-$C_6$-alkylcarbonylamino, $C_1$-$C_6$-haloalkyl-carbonylamino, carboxy, NH—C(O)—$NR^{x1}R^{x2}$, $NR^{x1}R^{x2}$,
$NR^{x1}R^{x2}$—$C_1$-$C_6$-alkylene, O—$NR^{x1}R^{x2}$, wherein $R^{x1}$ and $R^{x2}$ in the last 4 mentioned radicals are independently of each other hydrogen, $C_1$-$C_6$-alkyl, $C_1$-$C_6$-haloalkyl or $C_1$-$C_6$-alkoxy or $R^{x1}$ and $R^{x2}$ in the last 4 mentioned radicals together with the nitrogen atom form an N-bound 5-, 6- or
7-membered, saturated heterocycle which is unsubstituted or which carries 1, 2, 3 or 4 radicals selected from $C_1$-$C_4$-alkyl, $C_1$-$C_4$-haloalkyl,
$C_1$-$C_4$-hydroxyalkyl and $C_1$-$C_4$-alkoxy and wherein 2 radicals $R^x$, which are bound to adjacent carbon atoms of Ar may form a saturated or unsaturated 5- or 6-membered carbocyclic or heterocyclic ring, which itself may carry a radical $R^x$;
and physiologically tolerated acid addition salts and the N-oxides thereof.

Compounds of formula (I), wherein X is $S(O)_2$, are preferably selected from compounds, wherein at least one of the radicals $R^1$, $R^2$ and if present $R^5$ is different from hydrogen and $C_1$-$C_4$-alkyl.

The present invention also relates to a pharmaceutical composition which comprises at least one quinoline compound of the formula (I) and/or at least one physiologically tolerated acid addition salt of (I) and/or at least one N-oxide of (I), where appropriate together with physiologically acceptable carriers and/or auxiliary substances.

The present invention further relates to the use of a quinoline compound of the formula (I) and/or physiologically tolerated acid addition salts thereof and/or at least one N-oxide of (I), for preparing a pharmaceutical composition, optionally together with at least one physiologically acceptable carrier or auxiliary substance.

The compounds are selective 5-$HT_6$ receptor ligands. Thus the compounds are particularly suitable for the treatment of disorders of the central nervous system, addiction diseases or obesity, as these disorders and diseases are likely to respond to influencing by 5-$HT_6$ receptor ligands. Therefore the present invention also provides a method for treating disorders in mammals, said method comprising administering an effective amount of at least one compound of the formula (I) and/or at least one physiologically tolerated acid addition salt of (I) and/or at least one N-oxide of (I) to a subject in need thereof.

DETAILED DESCRIPTION OF THE INVENTION

The diseases which are susceptible to treatment with a quinoline compound of the formula I include, e.g., disorders and diseases of the central nervous system, in particular cognitive dysfunctions, such as a deficit in memory, cognition and learning, in particular associated with Alzheimer's disease, age-related cognitive decline and mild cognitive impairment, attention deficit disorder/hyperactivity syndrome (ADHD), personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowel Syndrome, diseases associated with neurodegeneration, such as stroke, spinal or head trauma and head injuries, such as hydrocephalus, drug addiction and obesity.

According to the invention, at least one quinoline compound of the general formula (I) having the meanings mentioned at the outset is used for treating the above mentioned indications. Provided the compounds of the formula (I) of a given constitution may exist in different spatial arrangements, for example if they possess one or more centers of asymmetry, polysubstituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formula (I) and/or of their salts and/or their N-oxides.

It is likewise possible to use physiologically tolerated salts of the compounds of the formula (I), especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, aromatic sulfonic acids, such as benzenesulfonic acid and toluenesulfonic acid, oxalic acid, maleic acid, fumaric acid, lactic acid, tartaric acid, adipic acid and benzoic acid. Other utilizable acids are described in Fortschritte der Arzneimittelforschung [Advances in drug research], Volume 10, pages 224 ff., Birkhäuser Verlag, Basel and Stuttgart, 1966.

It is likewise possible to use N-oxides of the compounds of the formula (I), if those compounds contain a basic nitrogen atom, such as the nitrogen atom of the quinoline moiety.

The organic moieties mentioned in the above definitions of the variables are—like the term halogen—collective terms for individual listings of the individual group members. The prefix $C_n$-$C_m$ indicates in each case the possible number of carbon atoms in the group.

The term "halogen" denotes in each case fluorine, bromine, chlorine or iodine, in particular fluorine, chlorine or bromine.

The term "$C_1$-$C_6$-alkyl" as used herein and in the alkyl moieties of $C_1$-$C_6$-hydroxyalkyl, $C_1$-$C_6$-alkoxy-$C_1$-$C_4$-alkyl, $C_1$-$C_6$-alkylthio, $C_1$-$C_6$-alkylsulfinyl, $C_1$-$C_6$-alkylsulfonyl, $C_1$-$C_6$-alkylcarbonyl, $C_1$-$C_6$-alkylcarbonylamino, $C_3$-$C_6$-cycloalkyl-$C_1$-$C_4$-alkyl, aryl-$C_1$-$C_4$-alkyl or hetaryl-$C_1$-$C_4$-alkyl denotes in each case a straight-chain or branched alkyl group having from 1 to 6 carbon atoms, preferably 1 to 4 carbon atoms. Examples of an alkyl group are methyl, ethyl, n-propyl, iso-propyl, n-butyl, 2-butyl, iso-butyl, tert-butyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

The term "$C_1$-$C_6$-haloalkyl" as used herein and in the haloalkyl moieties of $C_1$-$C_6$-haloalkylthio, $C_1$-$C_6$-haloalkylsulfinyl, $C_1$-$C_6$-haloalkylsulfonyl, $C_1$-$C_6$-haloalkylcarbonyl, $C_1$-$C_6$-haloalkylcarbonylamino denotes in each case a straight-chain or branched alkyl group having from 1 to 6 carbon atoms, wherein the hydrogen atoms of this group are partially or totally replaced with halogen atoms. Preferred haloalkyl moieties are selected from $C_1$-$C_4$-haloalkyl, especially preferred from $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluorethyl, 2,2,2-trichloroethyl, pentafluoroethyl and the like.

The term "$C_1$-$C_4$-alkylene" as used herein denotes a straight-chain or branched bivalent alkandiyl group having from 1 to 4 carbon atoms, examples including methylene, 1,1-ethylene (1,1-ethandiyl), 1,2-ethylene (1,2-ethandiyl), 1,1-propandiyl, 1,2-propandiyl, 2,2-propandiyl, 1,3-propandiyl, 1,1-butandiyl, 1,2-butandiyl, 1,3-butandiyl, 1,4-butandiyl, 2,3-butandiyl, 2,2-butanediyl. The term "linear $C_1$-$C_4$-alkylene" as used herein denotes a straight-chain bivalent alkandiyl group having from 1 to 4 carbon atoms, examples including methylene, 1,2-ethylene, 1,3-propandiyl and 1,4-butandiyl.

The term "$C_1$-$C_6$-alkoxy" as used herein and in the alkoxy moieties of $C_1$-$C_6$-alkoxy-$C_1$-$C_4$-alkyl denotes in each case a straight-chain or branched alkoxy group having from 1 to 6 carbon atoms, preferably 1 to 4 carbon atoms. Examples of an alkoxy group are methoxy, ethoxy, n-propoxy, iso-propoxy, n-butyloxy, 2-butyloxy, iso-butyloxy, tert-butyloxy, pentyloxy, 1-methylbutyloxy, 2-methylbutyloxy, 3-methylbutyloxy, 2,2-dimethylpropyloxy, 1-ethylpropyloxy, hexyloxy, 1,1-dimethylpropyloxy, 1,2-dimethylpropyloxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropyloxy, 1,2,2-trimethylpropyloxy, 1-ethyl-1-methylpropyloxy and 1-ethyl-2-methylpropyloxy.

The term "$C_1$-$C_6$-haloalkoxy" as used herein and in the haloalkoxy moieties of $C_1$-$C_6$-haloalkoxy-$C_1$-$C_4$-alkyl denotes in each case a straight-chain or branched alkoxy group having from 1 to 6 carbon atoms, wherein the hydrogen atoms of this group are partially or totally replaced with halogen atoms, in particular fluorine atoms. Preferred haloalkoxy moieties include $C_1$-$C_4$-haloalkoxy, in particular $C_1$-$C_2$-fluoroalkoxy, such as fluoromethoxy, difluoromethoxy, trifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and the like.

The term "$C_1$-$C_6$-hydroxyalkyl" is a straight-chain or branched alkyl group having from 1 to 6, especially 1 to 4 carbon atoms (=$C_1$-$C_4$ hydroxyalkyl), in particular 1 to 3 carbon atoms (=$C_1$-$C_3$ hydroxyalkyl), wherein one of the hydrogen atoms is replaced by a hydroxy group, such as in 2-hydroxyethyl or 3-hydroxypropyl.

The term "$C_1$-$C_6$-alkoxy-$C_1$-$C_4$-alkyl" is a straight-chain or branched alkyl group having from 1 to 4 carbon atoms, wherein one of the hydrogen atoms is replaced by a $C_1$-$C_6$-alkoxy group, such as in methoxymethyl, ethoxymethyl, propoxymethyl, 1-methoxyethyl, 1-ethoxyethyl, 2-methoxyethyl, 2-ethoxyethyl, 2-methoxypropyl, 2-ethoxypropyl, 3-methoxypropyl or 3-ethoxypropyl.

The term "$C_1$-$C_6$-haloalkoxy-$C_1$-$C_4$-alkyl" is a straight-chain or branched alkyl group having from 1 to 4 carbon atoms, wherein one of the hydrogen atoms is replaced by a $C_1$-$C_6$-haloalkoxy group.

The term "$C_3$-$C_6$-cycloalkyl" as used herein and in the cycloalkyl moieties of $C_3$-$C_6$-cycloalkyl-$C_1$-$C_4$-alkyl and $C_3$-$C_6$-halocycloalkyl denotes in each case a cycloaliphatic radical having from 3 to 6 C atoms, such as cyclopropyl, cyclobutyl, cyclopentyl and cyclohexyl. The cycloalkyl radical may be unsubstituted or may carry 1, 2, 3 or 4 $C_1$-$C_4$-alkyl radicals, preferably a methyl radical.

The term "$C_3$-$C_6$-halocycloalkyl" as used herein and in the halocycloalkyl moieties of $C_3$-$C_6$-halocycloalkyl-$C_1$-$C_4$-alkyl denotes in each case a cycloaliphatic radical having from 3 to 6 C atoms, such as cyclopropyl, cyclobutyl, cyclopentyl and cyclohexyl, wherein at least one hydrogen radical, e.g. 1, 2, 3, 4 or 5 hydrogen radicals are replaced by halogen, in particular fluorine. Examples include 1-fluorocyclopropyl, 2-fluorocyclopropyl, 2,2-difluorocyclopropyl, 1-fluorocyclobutyl, 2-fluorocyclobutyl, 2,2-difluorocyclobutyl, 3-fluorocyclobutyl, 3,3-difluorocyclobutyl, 1,3-difluorocyclobutyl etc, The term "$C_2$-$C_6$-alkenyl" as used herein and in the alkenyl moieties of $C_3$-$C_6$-haloalkenyl and aryl-$C_2$-$C_4$-alkenyl denotes in each case a singly unsaturated hydrocarbon radical having 2, 3, 4, 5 or 6 C-atoms, e.g. vinyl, allyl (2-propen-1-yl), 1-propen-1-yl, 2-propen-2-yl, methallyl (2-methylprop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl and the like.

The term "aryl" as used herein denotes in each case a carbocyclic radical selected from the group consisting of phenyl and phenyl fused to a saturated or unsaturated 5- or 6-membered carbocyclic ring, such as naphthyl, 1,2-dihydronaphthyl, 1,2,3,4-tetrahydronaphthyl, indenyl or indanyl, provided that in the fused rings aryl is bound via the phenyl part of the fused rings.

The term "hetaryl" as used herein denotes in each case a heterocyclic radical selected from the group consisting of monocyclic 5- or 6-membered heteroaromatic radicals comprising as ring members 1, 2 or 3 heteroatoms selected from N, O and S and 5- or 6-membered heteroaromatic ring fused to a phenyl ring or to a 5- or 6-membered heteroaromatic radical, where the heterocyclic ring comprises as ring members 1, 2 or 3 heteroatoms selected from N, O and S.

Examples of 5- or 6-membered heteroaromatic radicals include pyridyl, i.e. 2-, 3-, or 4-pyridyl, pyrimidinyl, i.e. 2-, 4- or 5-pyrimidinyl, pyrazinyl, pyridazinyl, i.e. 3- or 4-pyridazinyl, thienyl, i.e. 2- or 3-thienyl, furyl, i.e. 2- or 3-furyl, pyrrolyl, i.e. 2- or 3-pyrrolyl, oxazolyl, i.e. 2-, 3- or 5-oxazolyl, isoxazolyl, i.e. 3-, 4- or 5-isoxazolyl, thiazolyl, i.e. 2-, 3- or 5-thiazolyl, isothiazolyl, i.e. 3-, 4- or 5-isothiazolyl, pyrazolyl, i.e. 1-, 3-, 4- or 5-pyrazolyl, i.e. 1-, 2-, 4- or 5-imidazolyl, oxadiazolyl, e.g. 2- or 5-[1,3,4]oxadiazolyl, 4- or 5-(1,2,3-oxadiazol)yl, 3- or 5-(1,2,4-oxadiazol)yl, 2- or 5-(1,3,4-thiadiazol)yl, thiadiazolyl, e.g. 2- or 5-(1,3,4-thiadiazol)yl, 4- or 5-(1,2,3-thiadiazol)yl, 3- or 5-(1,2,4-thiadiazol)yl, triazolyl, e.g. 1H-, 2H- or 3H-1,2,3-triazol-4-yl, 2H-triazol-3-yl, 1H-, 2H-, or 4H-1,2,4-triazolyl and tetrazolyl, i.e. 1H- or 2H-tetrazolyl.

Examples of a 5- or 6-membered heteroaromatic ring fused to a phenyl ring or to a 5- or 6-membered heteroaromatic radical include benzofuranyl, benzothienyl, indolyl, indazolyl, benzimidazolyl, benzoxathiazolyl, benzoxadiazolyl, benzothiadiazolyl, benzoxazinyl, chinolinyl, isochinolinyl, purinyl, 1,8-naphthyridyl, pteridyl, pyrido[3,2-d]pyrimidyl or pyridoimidazolyl and the like. These fused hetaryl radicals may be bonded to the remainder of the molecule (more precisely to the X group) via any ring atom of 5- or 6-membered heteroaromatic ring or via a carbon atom of the fused phenyl moiety.

Examples of rings Ar, wherein 2 radicals $R^x$, which are bound to adjacent carbon atoms of Ar, form a saturated or unsaturated 5- or 6-membered carbocyclic or heterocyclic ring include 2,3-dihydrobenzofuranyl, 2,3-dihydroindolyl, dihydroisoindolyl, dihydrobenzoxazinyl, tetrahydroisochinolinyl, benzomorpholinyl, chromenyl, chromanyl, 1,2-dihydronaphthyl, 1,2,3,4-tetrahydronaphthyl, indenyl and indanyl.

The term "saturated or unsaturated heterocyclic ring" in each case denotes a 3- to 7-membered cyclic radical containing at least one hetero atom selected from the group consisting of N, O and S. Examples for such saturated or unsaturated 3- to 7-membered heterocyclic rings comprise saturated or unsaturated, aromatic or non-aromatic heterocyclic rings. Examples therefore include, apart from the above-defined 5- or 6-membered heteroaromatic radicals, aziridyl, diaziridinyl, oxiranyl, azetidinyl, azetinyl, di- and tetrahydrofuranyl, pyrrolinyl, pyrrolidinyl, oxopyrrolidinyl, pyrazolinyl, pyrazolidinyl, imidazolinyl, imidazolidinyl, oxazolinyl, oxazolidinyl, oxo-oxazolidinyl, isoxazolinyl, isoxazolidinyl, piperidinyl, piperazinyl, morpholinyl, thiomorpholinyl, oxothiomorpholinyl, dioxothiomorpholinyl and the like.

Examples for "N-bound 5- to 7-membered saturated heterocycle" are pyrrolidin-1-yl, piperidin-1-yl, piperazin-1-yl, morpholin-4-yl, imidazolidin-1-yl, oxazolidin-3-yl, thiazolidin-3-yl or hexahydrodiazepin-1-yl, especially piperidin-1-yl and morpholin-4-yl.

With regard to their ability to bind to the 5-HT$_6$ receptor preference is given to compounds of formula (I), wherein the variables Ar, A, X, n, m, $R^1$, $R^2$, $R^3$, $R^4$, $R^a$ and $R^b$ have the meanings given below.

The remarks made in the following with respect to preferred aspects of the invention, e.g. to preferred meanings of the variables of compound (I), to preferred compounds (I) and to preferred embodiments of the method or the use according to the invention, apply in each case on their own or to combinations thereof.

A first preferred embodiment of the invention relates to compounds of the formula (I), wherein R is a cyclic moiety, i.e. $R^1$ and $R^3$ together are linear $C_1$-$C_4$-alkylene, which may carry 1 or 2 radicals $R^6$; $R^1$ and $R^5$ together are a single bond or linear $C_1$-$C_4$-alkylene, which may carry 1 or 2 radicals $R^7$; or $R^3$ and $R^5$ together are linear $C_1$-$C_4$-alkylene, which may carry 1 or 2 radicals $R^8$.

More preferred are compounds of formula (I) wherein the radicals $R^1$ and $R^3$ together form a linear $C_1$-$C_4$-alkylene moiety, which may carry 1 or 2 radicals $R^6$, in particular 0 or 1 radicals $R^6$. Amongst these compounds, preference is given to those compounds of the formula I, wherein the moiety R

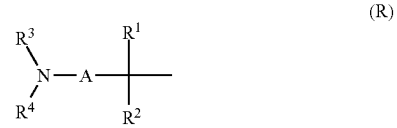

(R)

is a radical of the formulae $R^A$ or $R^B$:

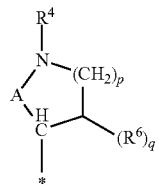

(R$^A$)

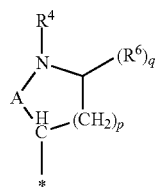

(R$^B$)

wherein A, $R^4$ and $R^6$ are as defined above, * indicates the binding site to the quinolinyl radical, p is 0, 1, 2 or 3 and q is 0 or 1. p is preferably 1 or 2. In the formulae $R^A$ and $R^B$, the radical A is in particular methylene, 1,2-ethylene, or $CH_2$—$CHR^5$. $R^5$ is preferably methyl. $R^6$ is preferably methyl or $R^5$ and $R^6$ together are 1,2-ethandiyl. $R^4$ is preferably hydrogen. Examples of radicals $R^A$ and $R^B$ include radicals of the formulae $R^{A1}$, $R^{A2}$, $R^{A3}$, $R^{A4}$, $R^{A5}$, $R^{A6}$ and $R^{A7}$:

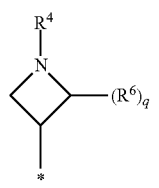

(R$^{A1}$)

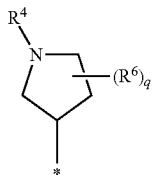

(R$^{A2}$)

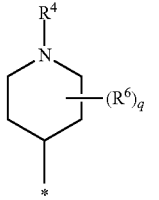

(R$^{A3}$)

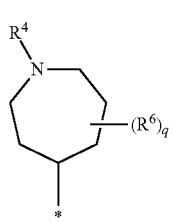

(R$^{A4}$)

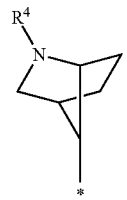

(R$^{A5}$)

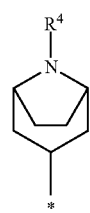

(R$^{A6}$)

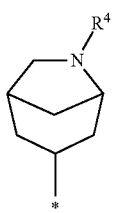

(R$^{A7}$)

wherein $R^4$ and $R^6$ are as defined above, * indicates the binding site to the quinolinyl radical and q is 0 or 1. $R^6$ is preferably methyl. $R^4$ is preferably hydrogen.

Particular preference is given to quinoline compounds of the formula I, wherein the moiety R is of the formulae $R^{A2}$, $R^{A3}$ or $R^{A4}$, wherein $R^4$ and $R^6$ are as defined above, and q is 0 or 1. In the formulae $R^{A2}$, $R^{A3}$ and $R^{A4}$ the radical $R^6$, if present, is preferably methyl. In the formulae $R^{A2}$, $R^{A3}$ and $R^{A4}$ the radical $R^4$ is preferably hydrogen.

Particular preference is further given to quinoline compounds of the formula I, wherein the moiety R is of the formulae $R^{A1}$, $R^{A2}$ or $R^{A3}$, wherein $R^4$ and $R^6$ are as defined above, and q is 0 or 1. In the formulae $R^{A1}$, $R^{A2}$ and $R^{A3}$ the radical $R^6$, if present, is preferably methyl. In the formulae $R^{A1}$, $R^{A2}$ and $R^{A3}$ the radical $R^4$ is preferably hydrogen.

A particular preferred embodiment of the invention relates to compounds of the formula I, wherein the moiety R is a radical of the formula $R^{A3}$:

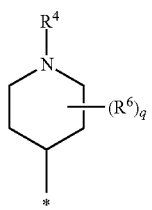

(R$^{A3}$)

wherein $R^4$ and $R^6$ are as defined above, * indicates the binding site to the quinolinyl radical and q is 0 or 1. $R^6$ is preferably methyl. $R^4$ is preferably hydrogen.

A second embodiment of the invention relates to compounds of the formula A, wherein the radical $R^1$ is hydrogen. Amongst these compounds, preference is given to those compounds of the formula I, wherein the moiety R is a radical of the formula $R^C$:

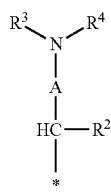

(R^C)

wherein A, $R^2$, $R^3$ and $R^4$ are as defined above, * indicates the binding site to the quinolinyl radical. In the formula $R^C$, the radical $R^2$ is preferably hydrogen. In the formula $R^C$, the radical A is in particular a single bond $CH_2$ or $CH_2CHR^5$, wherein $R^5$ is as defined above or preferably hydrogen or $R^3$ and $R^5$ together are $CH_2$, 1,2-ethandiyl or 1,3-propandiyl. In formula $R^C$, $R^3$ is preferably hydrogen or $C_1$-$C_4$-alkyl. In formula $R^C$, $R^4$ is preferably hydrogen. Examples of radicals $R^C$ include radicals of the formulae $R^{C1}$, $R^{C2}$, $R^{C3}$ and $R^{C4}$:

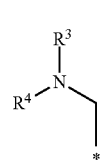

(R^{C1})

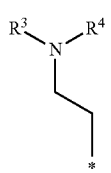

(R^{C2})

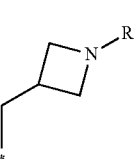

(R^{C3})

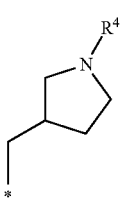

(R^{C4})

wherein $R^3$ and $R^4$ are as defined above. In these formulae, $R^4$ is preferably hydrogen or $C_1$-$C_4$-alkyl, in particular hydrogen.

A third embodiment of the invention relates to compounds of the formula I, wherein the radical $R^2$ is hydrogen A is a bivalent radical $CH_2CHR^5$ and wherein $R^1$ and $R^5$ are together linear $C_1$-$C_4$-alkylene, which may carry 1 or 2 radicals $R^7$. Amongst the compounds of the third embodiment, preference is given to those compounds of the formula I, wherein the moiety R is a radical of the formula $R^D$:

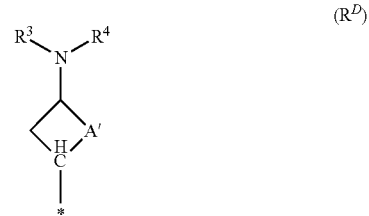

(R^D)

wherein A' is a single bond, $CH_2$, $CH_2CH_2$, $CHR^7$ or $CH_2CHR^7$, wherein $R^7$ is as defined above and wherein $R^7$ is in particular hydrogen. In the formula $R^D$, the radical A' is in particular a single bond $CH_2$ or $CH_2CH_2$. In formula $R^D$, $R^3$ is preferably hydrogen or $C_1$-$C_4$-alkyl, in particular hydrogen. In formula $R^D$, $R^4$ is preferably hydrogen. Examples of radicals $R^D$ include radicals of the formulae $R^{D1}$ and $R^{D2}$:

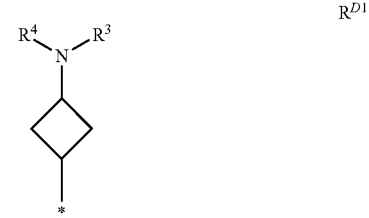

R^{D1}

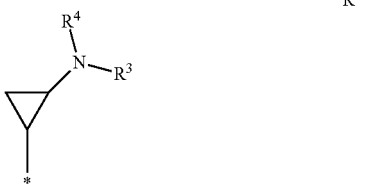

R^{D2} wherein $R^3$ and $R^4$ are as defined above and * indicates the binding site to the quinolinyl radical.

A particular preferred embodiment of the invention relates to compounds of the formula I, wherein X is $SO_2$.

Another embodiment of the invention relates to compounds of the formula I, wherein X is $CH_2$.

A further embodiment of the invention relates to compounds of the formula I, wherein X is a carbonyl group, i.e. X is C(=O).

In one preferred embodiment of the invention X is located in the 3-position of the quinolinyl moiety, i.e. this embodiment relates to compounds of the following formula Ia:

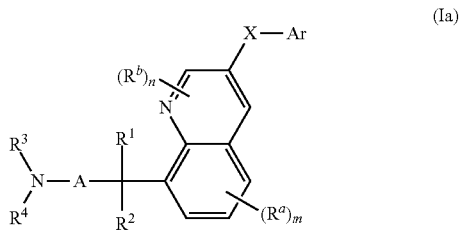

(Ia)

In another embodiment of the invention X is located in the 4-position of the quinolinyl moiety, i.e. this embodiment relates to compounds of the following formula Ib:

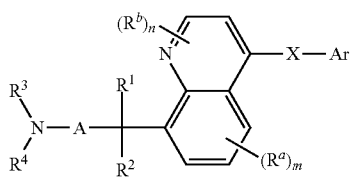

(Ib)

Amongst compounds Ia and Ib, preference is given to those compounds, wherein X is SO$_2$.

Amongst compounds Ia and Ib, preference is given to those compounds, wherein the moiety R is a moiety of the formula R$^A$ or R$^B$, in particular a moiety R$^{A2}$, R$^{A3}$ or R$^{A4}$ and more preferably a moiety R$^{A3}$, wherein q, R$^4$ and R$^6$ are as defined above.

Amongst compounds Ia and Ib, preference is also given to those compounds, wherein the moiety R is a moiety of the formula R$^C$, in particular a moiety R$^{C1}$, R$^{C2}$, R$^{C3}$ or R$^{C4}$, wherein R$^3$ and R$^4$ are as defined above.

Amongst compounds Ia and Ib, preference is also given to those compounds, wherein the moiety R is a moiety of the formula R$^D$, in particular a moiety R$^{D1}$ or R$^{D2}$, wherein R$^3$ and R$^4$ are as defined above.

Amongst compounds Ia and Ib, particular preference is given to those compounds Ia and Ib, wherein X is SO$_2$ and wherein R is a moiety of the formula R$^A$ or R$^B$, in particular a moiety R$^{A2}$, R$^{A3}$ or R$^{A4}$ and more preferably a moiety R$^{A3}$, wherein q, R$^4$ and R$^6$ are as defined above.

A very preferred embodiment of the invention relates to compounds of the following formula Ia.a:

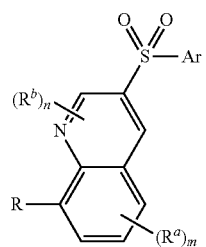

(Ia.a)

wherein n, m, Ar, R$^a$ and R$^b$ are as defined herein and wherein R is as defined above, e.g. a moiety of the formula R$^A$, R$^B$, R$^C$ or R$^D$, more preferably a moiety R$^A$ or R$^B$, in particular a moiety R$^{A2}$, R$^{A3}$ or R$^{A4}$ and most preferably a moiety R$^{A3}$.

Another preferred embodiment of the invention relates to compounds of the following formula Ia.b:

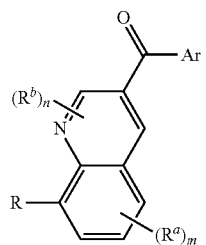

(Ia.b)

wherein n, m, Ar, R$^a$ and R$^b$ are as defined herein and wherein R is as defined above, e.g. a moiety of the formula R$^A$, R$^B$, R$^C$ or R$^D$, more preferably a moiety R$^A$ or R$^B$, in particular a moiety R$^{A2}$, R$^{A3}$ or R$^{A4}$ and most preferably a moiety R$^{A3}$.

A further preferred embodiment of the invention relates to compounds of the following formula Ia.c:

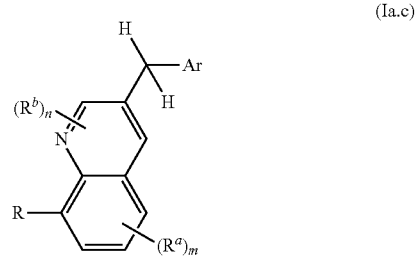

(Ia.c)

wherein n, m, Ar, R$^a$ and R$^b$ are as defined herein and wherein R is as defined above, e.g. a moiety of the formula R$^A$, R$^B$, R$^C$ or R$^D$, more preferably a moiety R$^A$ or R$^B$, in particular a moiety R$^{A2}$, R$^{A3}$ or R$^{A4}$ and most preferably a moiety R$^{A3}$.

A particularly preferred embodiment of the invention relates to compounds of the following formula Ia.a1:

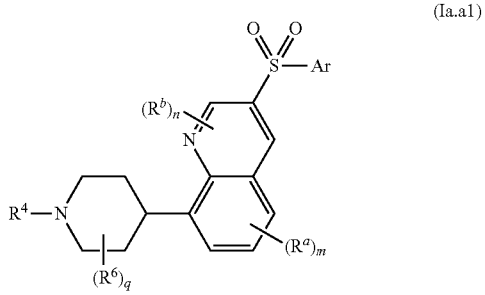

(Ia.a1)

wherein n, m, q, Ar, R$^4$, R$^6$, R$^a$ and R$^b$ are as defined herein. R$^4$ is in particular hydrogen. The variable q is in particular 0.

Another particularly preferred embodiment of the invention relates to compounds of the following formula Ia.a2:

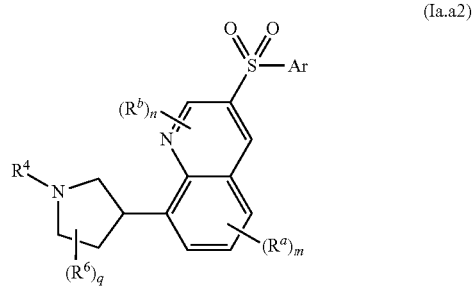

(Ia.a2)

wherein n, m, q, Ar, R$^4$, R$^6$, R$^a$ and R$^b$ are as defined herein. R$^4$ is in particular hydrogen. The variable q is in particular 0.

A further particularly preferred embodiment of the invention relates to compounds of the following formula Ia.a3:

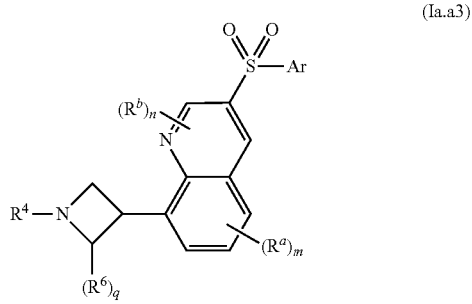

(Ia.a3)

wherein n, m, q, Ar, $R^4$, $R^6$, $R^a$ and $R^b$ are as defined herein. $R^4$ is in particular hydrogen. The variable q is in particular 0.

A further particularly preferred embodiment of the invention relates to compounds of the following formula Ia.a4:

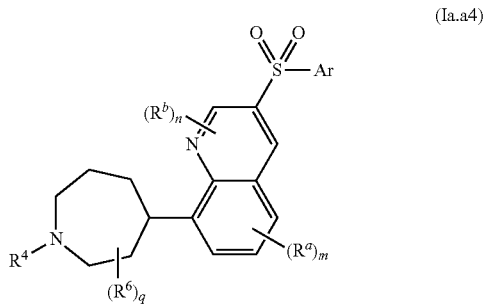

(Ia.a4)

wherein n, m, q, Ar, $R^4$, $R^6$, $R^a$ and $R^b$ are as defined herein. $R^4$ is in particular hydrogen. The variable q is in particular 0.

In the compounds of the formula I, and likewise in formulae Ia, Ib, Ia.a, Ia.b, Ia.c, Ia.a1, Ia.a2, Ia.a3 and Ia.a4, Ar is preferably a radical $Ar^1$, in particular a radical selected from phenyl, naphthyl, thienyl, pyridyl, pyrimidyl, pyrazolyl, imidazolyl, oxazolyl, isoxazolyl, thiazolyl, triazolyl, thiadiazolyl, quinolinyl, isoquinolinyl, tetrahydroisoquinolinyl, benzofuranyl, benzothiophenyl, benzoxazinyl, benzothiazolyl, benzoxadiazolyl, benzothiadiazolyl, benzomorpholinyl or indanyl, wherein the cyclic radical $Ar^1$ is unsubstituted or may carry 1, 2 or 3 substituents $R^x$ as defined herein. Likewise preferred are compounds of the formula I, wherein Ar is a radical $Ar^2$—$Ar^3$, wherein $Ar^2$ and $Ar^3$ are independently of each other selected from the group consisting of phenyl, thienyl, pyridyl, pyrimidyl, pyrazolyl, imidazolyl, oxazolyl, isoxazolyl, thiazolyl, triazolyl, thiadiazolyl, wherein the $Ar^1$ and $Ar^2$ are unsubstituted or may carry 1, 2 or 3 substituents $R^x$ as defined herein. In the radicals $Ar^2$—$Ar^3$, the radical $Ar^2$ is preferably selected from phenyl, pyridyl and thienyl, and the radical $Ar^3$ is preferably phenyl, thienyl, pyridyl, pyrimidyl, pyrazolyl, imidazolyl, oxazolyl, isoxazolyl, thiazolyl, triazolyl or thiadiazolyl, wherein $Ar^2$ and $Ar^3$ are unsubstituted or may carry 1, 2 or 3 substituents $R^x$ as defined herein. Likewise preferred are compounds of the formula I, wherein Ar is a radical $Ar^2$—O—$Ar^3$, wherein $Ar^2$ and $Ar^3$ are independently of each other selected from the group consisting of phenyl, thienyl, pyridyl, pyrimidyl, pyrazolyl, imidazolyl, oxazolyl, isoxazolyl, thiazolyl, triazolyl or thiadiazolyl, wherein $Ar^2$ and $Ar^3$ are unsubstituted or may carry 1, 2 or 3 substituents $R^x$ as defined herein. In the radicals $Ar^2$—$Ar^3$, the radical $Ar^2$ is preferably selected from phenyl, pyridyl and thienyl, and the radical $Ar^3$ is preferably phenyl, wherein $Ar^2$ and $Ar^3$ are unsubstituted or may carry 1, 2 or 3 substituents $R^x$ as defined herein.

In the compounds of the formula I, and likewise in formulae Ia, Ib, Ia.a, Ia.b, Ia.c, Ia.a1, Ia.a2, Ia.a3 and Ia.a4, Ar is more preferably phenyl, which is unsubstituted or may carry 1, 2 or 3 substituents $R^x$ as defined herein.

If $R^x$ is present, $R^x$ is preferably selected from halogen, CN, $C_1$-$C_4$-alkyl, $C_1$-$C_4$-haloalkyl, $C_1$-$C_4$-alkoxy, $C_1$-$C_4$-haloalkoxy, $C_3$-$C_6$-cycloalkyl, and a group $NR^{x1}R^{x2}$. More preferably $R^x$ is selected from halogen, $C_1$-$C_4$-haloalkyl, $C_1$-$C_4$-haloalkoxy, and a group $NR^{x1}R^{x2}$. Most preferably $R^x$ is selected from halogen, $C_1$-$C_4$-haloalkyl, or $C_1$-$C_4$-haloalkoxy.

In one embodiment $R^x$ is phenyl or phenoxy (i.e. Ar is $Ar^2$—$Ar^3$ or $Ar^2$—O—$Ar^3$ with $Ar^3$ being phenyl), wherein the phenyl radical in the 2 last-mentioned radicals is unsubstituted or may carry 1, 2 or 3 substituents selected from halogen, CN, $NO_2$, $C_1$-$C_4$-alkyl, $C_1$-$C_4$-haloalkyl, $C_1$-$C_4$-alkoxy, $C_1$-$C_4$-haloalkoxy.

In the compounds of the formula I, and likewise in formulae Ia, Ib, Ia.a, Ia.b, Ia.c, Ia.a1, Ia.a2, Ia.a3 and Ia.a4, m is preferably 0. If m is different from 0, $R^a$ is preferably selected from halogen, CN, $C_1$-$C_4$-alkyl, in particular methyl, $OCH_3$, $CF_3$, $CHF_2$, $OCHF_2$ and $OCF_3$.

In the compounds of the formula I, and likewise in formulae Ia, Ib, Ia.a, Ia.a1, Ia.a2 and Ia.a3, n is preferably 0. If m is different from 0, $R^b$ is preferably selected from halogen, CN, $C_1$-$C_4$-alkyl, in particular methyl, $OCH_3$, $CF_3$, $CHF_2$, $OCHF_2$ and $OCF_3$.

Examples of preferred compounds of the formula I are given in the following tables 1 to 6.

Table 1.

Compounds of formula I.a.a, wherein m and n are 0 and R is a moiety of the formula $R^{43}$ with q being 0, wherein and the variables Ar and $R^4$ have the meanings given in one of rows 1 to 110 of table A (compounds Ia.a1-1 to Ia.a1-110).

TABLE A

| | Ar | $R^4$ |
|---|---|---|
| 1 | phenyl | H |
| 2 | 2-fluorophenyl | H |
| 3 | 3-fluorophenyl | H |
| 4 | 2,3-difluorophenyl | H |
| 5 | 2,4-difluorophenyl | H |
| 6 | 2,5-difluorophenyl | H |
| 7 | 2,6-difluorophenyl | H |
| 8 | 3,4-difluorophenyl | H |
| 9 | 3,5-difluorophenyl | H |
| 10 | 2-chlorophenyl | H |
| 11 | 3-chlorophenyl | H |
| 12 | 2-tolyl | H |
| 13 | 3-tolyl | H |
| 14 | 2-isopropylphenyl | H |
| 15 | 3-isopropylphenyl | H |
| 16 | 2-difluoromethylphenyl | H |
| 17 | 3-difluoromethylphenyl | H |
| 18 | 2-trifluoromethylphenyl | H |
| 19 | 3-trifluoromethylphenyl | H |
| 20 | biphenyl-2-yl | H |
| 21 | biphenyl-3-yl | H |
| 22 | 2-methoxyphenyl | H |
| 23 | 3-methoxyphenyl | H |
| 24 | 2-difluoromethoxyphenyl | H |
| 25 | 3-difluoromethoxyphenyl | H |
| 26 | 2-trifluoromethoxyphenyl | H |
| 27 | 3-trifluoromethoxyphenyl | H |
| 28 | 2-phenoxyphenyl | H |
| 29 | 3-phenoxyphenyl | H |
| 30 | 4-(oxazol-5-yl)phenyl | H |
| 31 | 3-(pyrrolidin-1-yl)phenyl | H |
| 32 | 1-naphthyl | H |
| 33 | 2-naphthyl | H |
| 34 | pyridin-2-yl | H |

TABLE A-continued

| | Ar | R⁴ |
|---|---|---|
| 35 | pyridin-3-yl | H |
| 36 | pyridin-4-yl | H |
| 37 | 2-(pyrrolidin-1-yl)pyridin-4-yl | H |
| 38 | 6-morpholinylpyridin-3-yl | H |
| 39 | 6-phenoxypyridin-3-yl | H |
| 40 | thien-2-yl | H |
| 41 | 5-methylthien-2-yl | H |
| 42 | 5-(pyridin-2-yl)thien-2-yl | H |
| 43 | 5-(2-methylthiazol-4-yl)-thien-2-yl | H |
| 44 | 5-chloro-3-methyl-benzo[b]thien-2-yl | H |
| 45 | 2-methylthiazol-5-yl | H |
| 46 | 2,4-dimethyl-thiazol-5-yl | H |
| 47 | 4-methylthiazol-2-yl | H |
| 48 | 5-methylthiazol-2-yl | H |
| 49 | 3,5-dimethylisoxazol-4-yl | H |
| 50 | 1-methylimidazol-4-yl | H |
| 51 | benzothiazol-7-yl | H |
| 52 | 4-methylbenzomorpholin-8-yl | H |
| 53 | quinolin-8-yl | H |
| 54 | isoquinolin-4-yl | H |
| 55 | 2,1,3-benzoxdiazol-4-yl | H |
| 56 | phenyl | n-propyl |
| 57 | 2-fluorophenyl | n-propyl |
| 58 | 3-fluorophenyl | n-propyl |
| 59 | 2,3-difluorphenyl | n-propyl |
| 60 | 2,4-difluorophenyl | n-propyl |
| 61 | 2,5-difluorophenyl | n-propyl |
| 62 | 2,6-difluorophenyl | n-propyl |
| 63 | 3,4-difluorophenyl | n-propyl |
| 64 | 3,5-difluorophenyl | n-propyl |
| 65 | 2-chlorophenyl | n-propyl |
| 66 | 3-chlorophenyl | n-propyl |
| 67 | 2-tolyl | n-propyl |
| 68 | 3-tolyl | n-propyl |
| 69 | 2-isopropylphenyl | n-propyl |
| 70 | 3-isopropylphenyl | n-propyl |
| 71 | 2-difluoromethylphenyl | n-propyl |
| 72 | 3-difluoromethylphenyl | n-propyl |
| 73 | 2-trifluoromethylphenyl | n-propyl |
| 74 | 3-trifluoromethylphenyl | n-propyl |
| 75 | biphenyl-2-yl | n-propyl |
| 76 | biphenyl-3-yl | n-propyl |
| 77 | 2-methoxyphenyl | n-propyl |
| 78 | 3-methoxyphenyl | n-propyl |
| 79 | 2-difluoromethoxyphenyl | n-propyl |
| 80 | 3-difluoromethoxyphenyl | n-propyl |
| 81 | 2-trifluoromethoxyphenyl | n-propyl |
| 82 | 3-trifluoromethoxyphenyl | n-propyl |
| 83 | 2-phenoxyphenyl | n-propyl |
| 84 | 3-phenoxyphenyl | n-propyl |
| 85 | 4-(oxazol-5-yl)phenyl | n-propyl |
| 86 | 3-(pyrrolidin-1-yl)phenyl | n-propyl |
| 87 | 1-naphthyl | n-propyl |
| 88 | 2-naphthyl | n-propyl |
| 89 | pyridin-2-yl | n-propyl |
| 90 | pyridin-3-yl | n-propyl |
| 91 | pyridin-4-yl | n-propyl |
| 92 | 2-(pyrrolidin-1-yl)pyridin-4-yl | n-propyl |
| 93 | 6-morpholinylpyridin-3-yl | n-propyl |
| 94 | 6-phenoxypyridin-3-yl | n-propyl |
| 95 | thien-2-yl | n-propyl |
| 96 | 5-methylthien-2-yl | n-propyl |
| 97 | 5-(pyridin-2-yl)thien-2-yl | n-propyl |
| 98 | 5-(2-methylthiazol-4-yl)-thien-2-yl | n-propyl |
| 99 | 5-chloro-3-methyl-benzo[b]thien-2-yl | n-propyl |
| 100 | 2-methylthiazol-5-yl | n-propyl |
| 101 | 2,4-dimethyl-thiazol-5-yl | n-propyl |
| 102 | 4-methylthiazol-2-yl | n-propyl |
| 103 | 5-methylthiazol-2-yl | n-propyl |
| 104 | 3,5-dimethylisoxazol-4-yl | n-propyl |
| 105 | 1-methylimidazol-4-yl | n-propyl |

TABLE A-continued

| | Ar | R⁴ |
|---|---|---|
| 106 | benzothiazol-7-yl | n-propyl |
| 107 | 4-methylbenzomorpholin-8-yl | n-propyl |
| 108 | quinolin-8-yl | n-propyl |
| 109 | isoquinolin-4-yl | n-propyl |
| 110 | 2,1,3-benzoxdiazol-4-yl | n-propyl |

Table 2.

Compounds of formula I.a.a, wherein m and n are 0 and R is a moiety of the formula $R^{43}$ with q being 1 and $R^6$ being methyl which is located in the 2-position of the piperidine ring, wherein and the variables Ar and $R^4$ have the meanings given in one of rows 1 to 110 of table A (compounds Ia.a1-111 to Ia.a1-220).

Table 3.

Compounds of formula I.a.a, wherein m and n are 0 and R is a moiety of the formula $R^{43}$ with q being 1 and $R^6$ being methyl which is located in the 3-position of the piperidine ring, wherein and the variables Ar and $R^4$ have the meanings given in one of rows 1 to 110 of table A (compounds Ia.a1-221 to Ia.a1-330).

Table 4.

Compounds of formula I.a.a, wherein m and n are 0 and R is a moiety of the formula $R^{42}$ with q being 0, wherein and the variables Ar and $R^4$ have the meanings given in one of rows 1 to 110 of table A (compounds Ia.a2-1 to Ia.a2-110).

Table 5.

Compounds of formula I.a.a, wherein m and n are 0 and R is a moiety of the formula $R^{41}$ with q being 0, wherein and the variables Ar and $R^4$ have the meanings given in one of rows 1 to 110 of table A (compounds Ia.a3-1 to Ia.a3-110).

Table 6.

Compounds of formula I.a.a, wherein m and n are 0 and R is a moiety of the formula $R^{44}$ with q being 0, wherein and the variables Ar and $R^4$ have the meanings given in one of rows 1 to 110 of table A (compounds Ia.a-4-1 to Ia.a-4-110).

Compounds of the formula I according to the present invention can be obtained as outlined in the synthetic routes below.

1. General Synthetic Pathways

Compounds of the formula I can be prepared e.g. starting from suitable 8-halo substituted quinoline compounds of the formula II and amines III by a transition metal catalyzed cross-coupling as depicted in scheme 1:

Scheme 1:

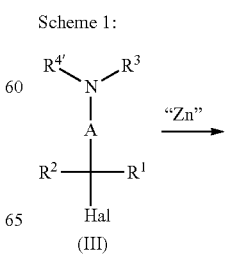

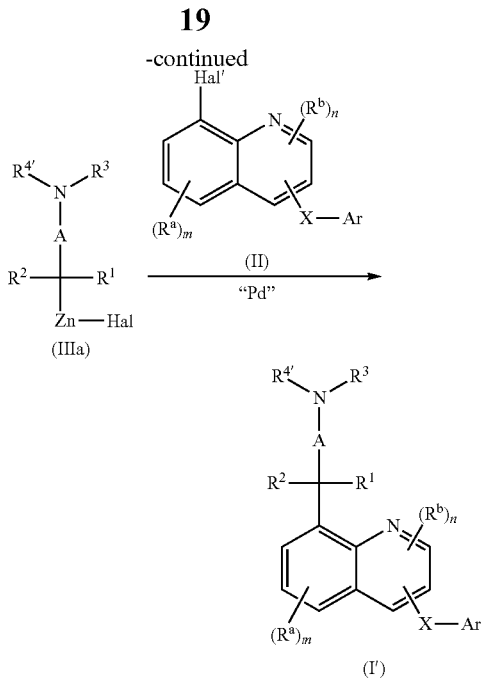

In scheme 1 the variables $R^1$, $R^2$, $R^3$, A, $R^a$, $R^b$, X, Ar, m and n are as defined herein. $R^{4'}$ has one of the meanings given for $R^4$ different from hydrogen or a suitable N-protecting group, e.g. Boc, and Hal and Hal' are Br or I. According to scheme 1 the halogen compound III is converted into a organozinc compound IIIa according to standard processes, e.g. by the process described in Tetrahedron 1987, 43, 2203-2212; J. Org. Chem. 1988, 53, 2390-2392. The organozinc compound is subsequently reacted in a Negeshi type Pd(0)-mediated cross coupling reaction with an appropriate 8-haloquinoline compound II to give the 8-substituted compound I' by analogy to the method described in Synlett 1998, 4, 379-380; J. Am. Chem. Soc. 2003, 125, 12527-12530. Alternatively, the intermediately generated organozinc compound IIIa can be transmetallized, e.g. with CuCN*2LiCl, and subsequent reacted with a 8-haloquinoline compound of formula II.

If $R^{4'}$ is a suitable N-protecting group, compounds of the formula I, wherein $R^4$ is hydrogen can be obtained from compounds of the formula I' by cleavage of the N—$R^{R4'}$-bond, In case of $R^{4'}$ being Boc, cleavage can be achieved by treatment with trifluoroacetic acid.

If in the resulting quinoline compound I' the radical $R^{4'}$ is not the desired radical $R^4$ but a precursor thereof, the compound can be modified as outlined below to obtain the desired substituent $R^4$. A precursor is a radical which can be easily removed and replaced by the desired group $R^4$ or which can be modified to give $R^4$. The precursor can also be an N-protective group (PG), such as butyloxycarbonyl (Boc), benzyloxycarbonyl (Cbz), 9-fluorenylmethoxycarbonyl (Fmoc), triphenylmethyl (Trt), nitrobenzenesulfenyl (Nps), allyl and benzyl.

If $R^{4'}$ is allyl, the allyl group can be cleaved to obtain a compound of the formula I, wherein $R^4$ is hydrogen. The cleavage of the allyl group is achieved, for example, by reacting a compound I' with $R^{4'}$=allyl with an allyl trapping agent, such as mercaptobenzoic acid or 1,3-dimethylbarbituric acid, in the presence of catalytic quantities of palladium (0) compounds or palladium compounds which are able to form a palladium(0) compound under reaction conditions, e.g. palladium dichloride, tetrakis(triphenylphosphine)palladium(0) or tris(dibenzylideneacetone)dipalladium(0), advantageously in combination with phosphine ligands, e.g. triarylphosphines, such as triphenylphosphine, trialkylphosphines, such as tributylphosphine, and cycloalkylphosphines, such as tricyclohexylphosphine, and especially with phosphine chelate ligands, such as 2,2'-bis(diphenylphosphino)-1,1'-binaphthyl or 1,4-bis(diphenylphosphino)butane, applying methods known to a skilled person (with regard to eliminating N-allyl in the presence of mercaptobenzoic acid, see WO 94/24088; with regard to eliminating in the presence of 1,3-dimethylbarbituric acid, see J. Am. Chem. Soc. 2001, 123 (28), pp. 6801-6808 and J. Org. Chem. 2002, 67(11) pp. 3718-3723). Alternatively, the cleavage of N-allyl can also be effected by reacting compound I' with $R^{4'}$ being allyl in the presence of rhodium compounds, such as tris(triphenylphosphine)chlororhodium(I), by analogy to the methods described in J. Chem. Soc., Perkin Transaction I: Organic and Bio-Organic Chemistry 1999 (21) pp. 3089-3104 and Tetrahedron Asymmetry 1997, 8(20), pp. 3387-3391).

If $R^{4'}$ is benzyl, this substituent may also be cleaved to obtain a compound I wherein $R^4$ is H. The reaction conditions for the cleavage are known in the art. Typically, the benzyl group is removed by a hydrogenation reaction in the presence of a suitable Pd catalyst, such as Pd on carbon or palladium hydroxide.

$R^{4'}$ can also be a protective group. The protective group may be removed to yield a compound I, wherein $R^{4'}$ is hydrogen. Suitable protective groups are known in the art and are, for example, selected from tert-butoxycarbonyl (Boc), benzyloxycarbonyl (Cbz), 9-fluorenylmethoxycarbonyl (Fmoc), triphenylmethyl (Trt) and nitrobenzenesulfenyl (Nps). A preferred protective group is Boc. The protective groups can be removed by known methods, such as treatment of the protected amine with an acid, e.g. halogen acid, such as HCl or HBr, formic acid or trifluoroacetic acid, or by hydrogenation, optionally in the presence of a Pd catalyst.

The resulting compound I, wherein $R^4$ is H, can then be reacted, in a known manner, in the sense of an alkylation, with a compound $R^4$—X. In this compound, $R^4$ is $C_1$-$C_4$-alkyl, $C_3$-$C_6$-cycloalkyl, $C_1$-$C_4$-haloalkyl, $C_1$-$C_4$-alkoxy-$C_1$-$C_4$-alkyl, aryl-$C_1$-$C_4$-alkyl, hetaryl-$C_1$-$C_4$-alkyl or $C_3$-$C_6$-cycloalkyl-$C_1$-$C_4$-alkyl and X is a nucleophilically displaceable leaving group, e.g. halogen, trifluoromethylsulfonate, alkylsulfonate, arylsulfonate, alkyl sulfate and the like. The reaction conditions which are required for the alkylation have been disclosed, e.g. in Bioorganic and Medicinal Chemistry Lett. 2002, 12 (7), pp. 2443-2446 and also 2002, 12 (5), pp. 1917-1919.

The alkylation can also be achieved, in the sense of a reductive amination, by reacting the compound I, wherein $R^4$=H, with a suitable ketone or aldehyde in the presence of a reducing agent, e.g. in the presence of a borohydride such as sodium borohydride, sodium cyanoborohydride or sodium triacetoxyborohydride. The skilled person is familiar with the reaction conditions which are required for a reductive amination, e.g. from Bioorganic and Medicinal Chemistry Lett. 2002, 12 (5), pp. 795-798 and 12 (7) pp. 1269-1273.

In case $R^4$ is hydrogen, the compound I can also be reacted with an acyl halide to obtain a compound of the formula I wherein $R^4$ is formyl or $C_1$-$C_4$-alkylcarbonyl. The carbonyl group in these compounds can be reduced with diborane to obtain compounds of the general formula I, wherein $R^4$ is $C_2$-$C_5$-alkyl. The carbonyl group can also be reacted with a fluorinating agent to obtain a compound I wherein $R^4$ is 1,1-difluoroalkyl. Acylation and reduction can be achieved by standard methods, which are discussed in Jerry March, Advanced Organic Chemistry, 3rd ed. J. Wiley & Sons, New York 1985, p. 370 and 373 (acylation) and p. 1099 f. and in the literature cited in this publication (with regard to acylation, see also Synth. Commun. 1986, 16, p. 267, and with regard to reduction, see also J. Heterocycl. Chem. 1979, 16, p. 1525).

Compounds of the formula I, wherein the moiety R is a radical of the formula $R^A$ or $R^B$ with $R^4$ being hydrogen can be prepared e.g. starting from suitable 8-halo substituted quinoline compounds of the formula II by a transition metal catalyzed cross-coupling with a boronic compound IIIa and subsequent hydrogenation and deprotection, as depicted in scheme 2:

Scheme 2:

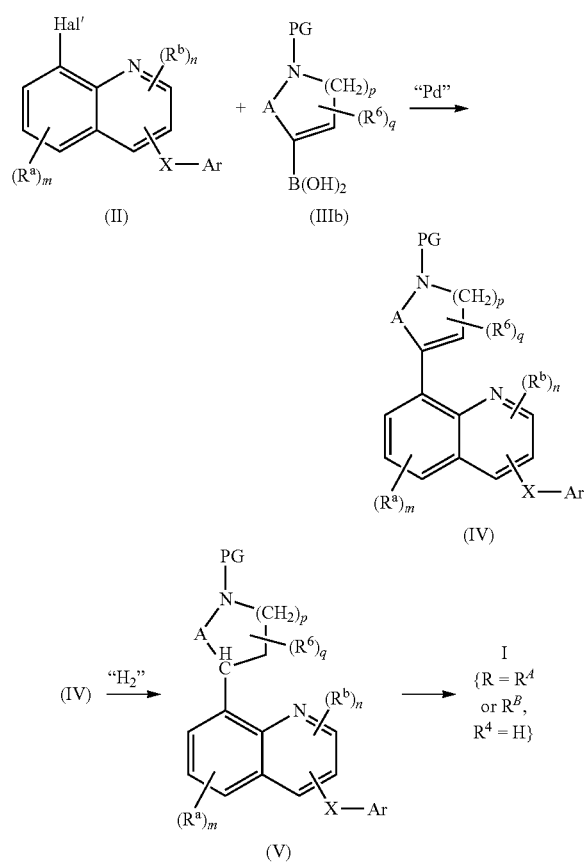

In scheme 2, the variables $R^6$, A, p, q, $R^a$, $R^b$, X, Ar, m and n are as defined herein. PG is suitable N-protecting group, e.g. BOC, and Hal and Hal' are Br or I. The 8-quinoline compound II is reacted under conditions of Suzuki coupling reaction with a boronic acid IIIb in the presence of a palladium catalyst to give a compound IV intermediate. Compound IV can then be reduced under conditions of catalytic hydrogenation to give the compound V. If the hydrogenation is carried out under chiral conditions, e.g. by using chiral catalysts, the enantiomerically pure phenylpyrrolidine compounds can be obtained. Chiral hydrogenation catalysts are well known in the art and are e.g. described in Jerry March, Advanced Organic Chemistry, John Wiley, 3$^{rd}$ edition. Dependent on the choice of protecting group PG, the free amino compound I ($R^4$=H) can be obtained by subsequent deprotection (e.g. TFA for BOC).

Compounds of the formula I, wherein the moiety R is a radical of the formula $R^{A2}$ can be prepared according to the method depicted in scheme 3:

Scheme 3:

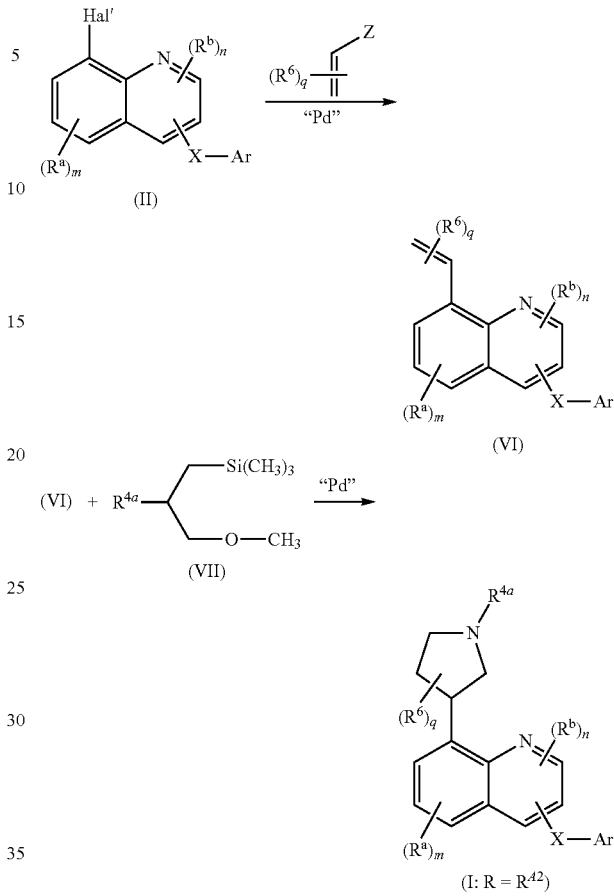

In scheme 3, the variables $R^6$, q, $R^a$, $R^b$, X, Ar, m and n are as defined herein. Z is a radical SnR$_3$ with R being $C_1$-$C_4$-alkyl. $R^{4a}$ has one of the meanings of $R^4$ different from H or is cleavable group, e.g. benzyl, and Hal' is Br or I. Key step is a [3+2] dipolar cycloaddition of a non-stabilized azomethine ylid to an 8-alkenylquinoline derivative VI to yield compound V. This procedure is generally described in J. Org. Chem. 1987, 52, 235. The precursor of the ylid, the amine VII, is commercially available or can be synthesized from NH$_2$(PG), (CH$_3$)$_3$SiCH$_2$Cl and HCHO in the presence of methanol.

The 8-alkenyl-quinoline compound (VI) can be synthesized e.g. by a Stille coupling of an 8-halogeno quinoline II, e.g. iodo, with the corresponding alkenyl tributyl stannate, such as vinyl or isobutenyl tributyl stannate, in the presence of an appropriate Pd coupling catalyst, e.g. tetrakistriphenylphosphine palladium(0) (see, e.g. Tetrahedron, 2003, 59 (34), 6545 and Bioorg. Med. Chem. 1999, 7 (5), 665). By choosing a special Stille isomer (e.g. cis- or trans-isobutenyl tributyl stannate), the corresponding cis- or trans alkyl phenyl pyrrolidine can be prepared selectively.

Alternatively, the 8-alkenyl-aromatic compound (VI) can be prepared by a Wittig reaction of the corresponding 8-formylquinoline derivative with a Wittig reagent such as PPh$_3$=CHR (R is H, or $C_1$-$C_3$-alkyl). Conditions for the Wittig reaction are well known in the art and are, e.g. discussed in Jerry March, Advanced Organic Chemistry, John Wiley, 3$^{rd}$ edition, page 845 ff.

The group $R^{4a}$ of the precursor amine VII advantageously corresponds either to the desired group $R^4$ of the final compound I or is alternatively a cleavable group, such as benzyl, which can be removed by catalytic hydrogenation to give the compound I with R=$R^{A2}$ and $R^4$=H.

Compounds of the formula I, wherein the moiety R is a radical of the formula $R^{A2}$ can also be prepared according to the method depicted in scheme 4:

Scheme 4:

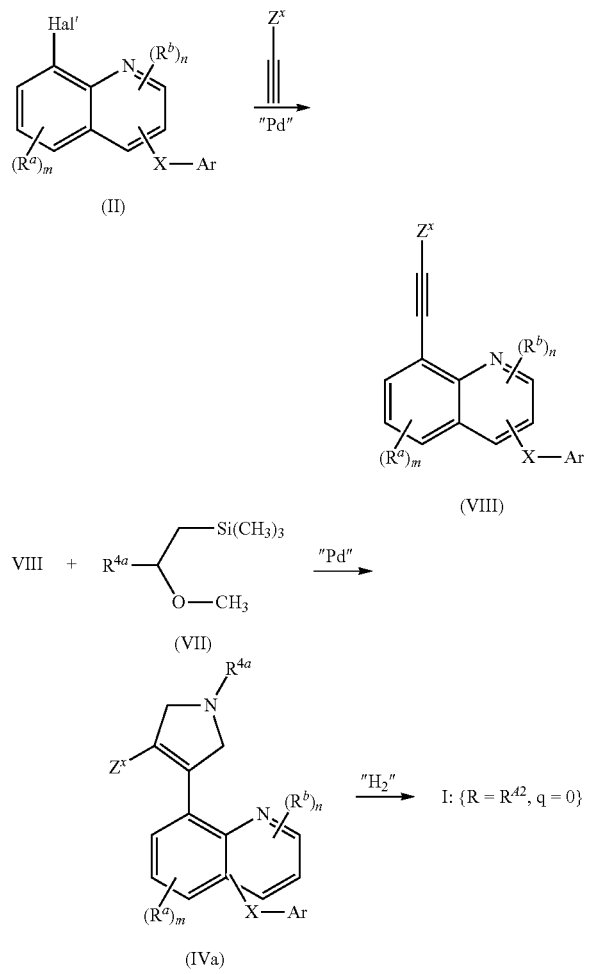

Scheme 5:

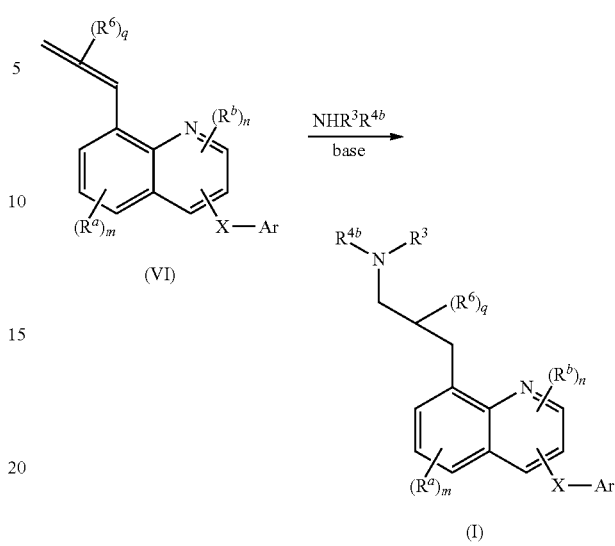

In scheme 5, the variables $R^6$, q, $R^a$, $R^b$, X, Ar, m and n are as defined herein. $R^{4b}$ has one of the meanings of $R^4$ different from H or is N-protecting group, e.g. benzyl or Boc. According to scheme 5, the 8-alkenyl-quinoline compound VI is treated with an appropriate amine $HNR^3R^{4b}$ in the presence of a strong base such n-butyl lithium (BuLi) or sodium hydride in an aprotic polar solvent such as tetrahydrofuran (THF) or N,N-dimethyl formamide (DMF) to give after workup the desired Michael addition product I.

Compounds of the formula I, wherein the moiety R is a radical of the formula $R^{C1}$ can be prepared starting from the compound II according to the method depicted in scheme 6:

Scheme 6:

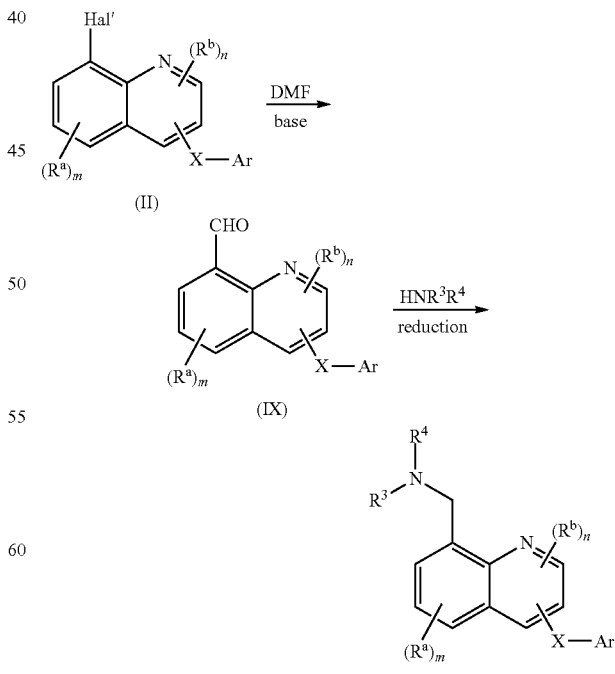

In scheme 4, the variables $R^a$, $R^b$, X, Ar, m and n are as defined herein. $Z^x$ is hydrogen, $C_1$-$C_4$-alkyl or $SiR_3$ with R being $C_1$-$C_4$-alkyl. $R^{4a}$ has one of the meanings of $R^4$ different from H or is cleavable group, e.g. benzyl, and Hal' is Br or I. Key step is a [3+2] dipolar cycloaddition of a non-stabilized azomethine ylid to an 8-alkynylquinoline derivative VIII to yield compound IVa (see, e.g., Tetrahedron 1996, 52, 59). IVa is then hydrogenated to the corresponding pyrrolidine compound I (R=$R^{A2}$) Optionally the moiety $Z^x$ is removed. If the hydrogenation is carried out under chiral conditions, e.g. by using chiral catalysts, the enantiomerically pure phenylpyrrolidine compounds can be obtained. Chiral hydrogenation catalysts are well known in the art and are e.g. described in Jerry March, Advanced Organic Chemistry, John Wiley, 3$^{rd}$ edition.

Compounds of the formula I, wherein the moiety R is a radical of the formula $R^{C2}$ can be prepared starting from the compound VI according to the method depicted in scheme 5:

In scheme 6, the variables $R^3$, $R^4$, $R^a$, $R^b$, X, Ar, m and n are as defined herein. Hal' is bromine or iodine. According to scheme 6, the 8-halo-quinoline compound II is reacted with DMF and appropriate base such BuLi or NaH in a aprotic solvent such as THF or DMF to give the formyl compound IX. Compound IX is then subjected to a reductive amination with amine $HNR^3R^4$ to give the desired amino methyl quinoline compound. Reductive amination is usually performed in the presence of a suitable base (e.g. $Na_2CO_3$) and reduction can be achieved by a variety of chemical reduction or catalytic hydrogenation techniques familiar to those skilled in the art.

Compounds of the formula I, wherein X is $CH_2$ may also be prepared starting from 3- or 4-haloquinoline compounds of the formula X as depicted in scheme 7:

Scheme 7:

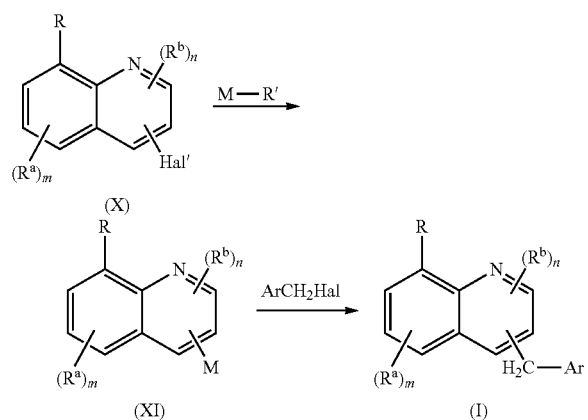

In scheme 7, the variables R, $R^a$, $R^b$, Ar, m and n are as defined herein. Hal and Hal' are bromine or iodine. R' is alkyl. M is lithium or Mg-Hal. According to scheme 7, a 3- or 4-haloquinoline compound X is treated with an alkyl metal compound M-R such as BuLi or MeMgBr in an aprotic ether solvent such as diethylether, methyl-tert.-butylether, THF or dioxan to give an intermediate metallated compound XI. Compound XI is then subjected to an alkylation with a suitable arylmethyl halide $ArCH_2Hal$ to give the desired 3- or 4-substituted quinoline. This reaction sequence can also be accomplished earlier in the synthetic route prior to the introduction of the 8-alkyl amino substituent. Compound X can be prepared by a rearrangement of the chemical transformations outlined in Schemes 1 to 6 in a manner well known to a person skilled in the art.

Compounds of the formula I, wherein X is C(=O) may also be prepared starting from 3- or 4-haloquinoline compounds of the formula X as depicted in scheme 7:

Scheme 8:

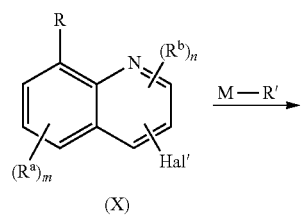

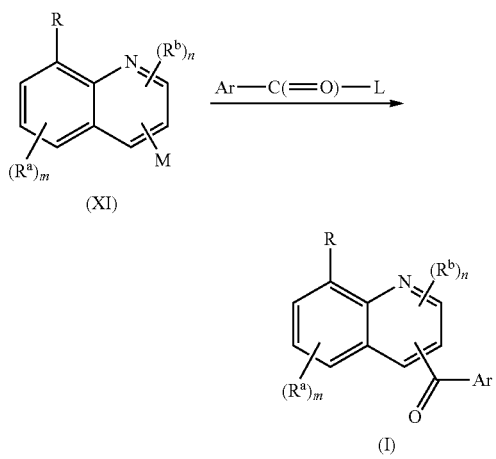

In scheme 8, the variables R, $R^a$, $R^b$, Ar, m and n are as defined herein. Hal' is bromine or iodine. R' is alkyl. M is lithium or Mg-Hal. L is a suitable leaving group, e.g. halogen (aroyl halide), O-alkyl (aroyl ester) or a Weinreb amide residue. According to scheme 8, a 3- or 4-haloquinoline compound X is treated with an alkyl metal compound M-R such as BuLi or MeMgBr in an aprotic ether solvent such as diethylether, methyl-tert.-butylether, THF or dioxane to give an intermediate metallated compound XI. Compound XI is then subjected to an acylation with a suitable aroyl compound Ar—C(=O)-L to give the desired 3- or 4-substituted quinoline. This reaction sequence can also be accomplished earlier in the synthetic route prior to the introduction of the 8-alkyl amino substituent.

The 8-haloquinoline compounds of the formula II are commercially available or they can be prepared according to routine techniques of organic synthesis, which are well known to a person skilled in the art. Compounds of the formula II, wherein X is $S(O)_2$ can be prepared e.g. starting from 8-nitroquinoline compounds of the formula XII as depicted in scheme 9.

Scheme 9:

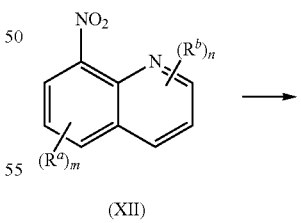

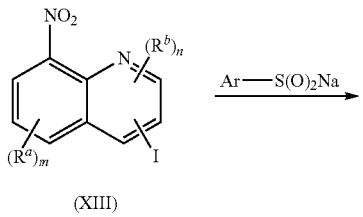

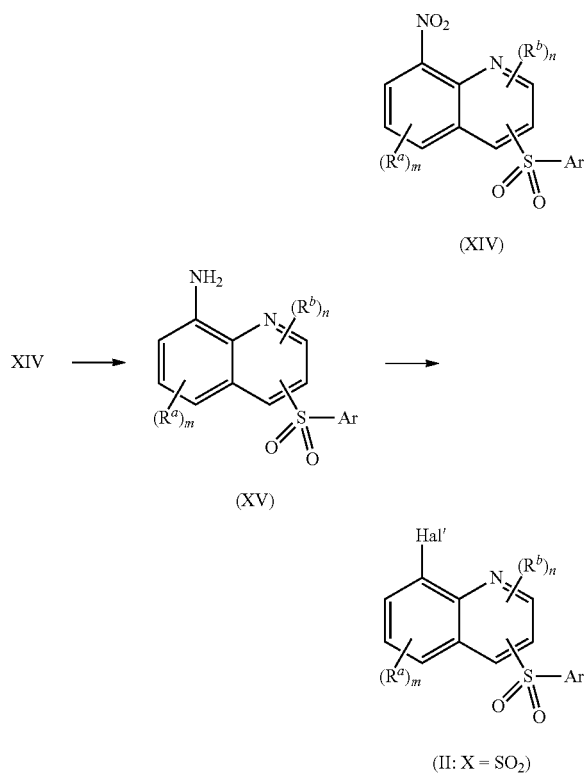

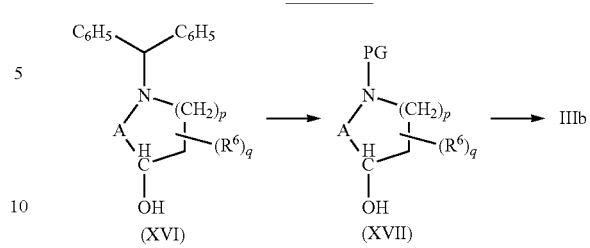

Starting from a benzhydryl compound XVI, e.g. 1-benzhydryl-azetidin-3-ol compound, a Pd-mediated deprotection is performed to yield the free amine (Tetrahedron 2002, 58, 9865-9870), Then, a protective group PG is introduced (e.g. carbamate formation if PG is BOC) to yield compound XVII. Subsequent halogenation generates the iodine compound IIIb that is susceptible to undergo Zn insertion (Tetrahedron 1987, 43, 2203-2212; J. Org. Chem. 1988, 53, 2390-2392). The thus obtainable organozinc compound can be used in synthetic routes as outlined above in scheme 1. The synthesis of azetidin-3-ol compounds has for instance been described in J. Med. Chem. 1994, 37, 4195-4210 or Helvetica Chimica Acta 1995, 78, 1238-1246.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002.

The acid addition salts of compounds I are prepared in a customary manner by mixing the free base with a corresponding acid, where appropriate in solution in an organic solvent, for example acetonitrile, a lower alcohol, such as methanol, ethanol or propanol, an ether, such as diethyl ether, methyl tert-butyl ether or diisopropyl ether, a ketone, such as acetone or methyl ethyl ketone, an ester, such as ethyl acetate, mixtures thereof as well as mixtures thereof with water.

The compound of the invention can be a 5-$HT_6$ receptor agonist, including partial agonistic activity, or a 5-$HT_6$ receptor antagonist, including inverse agonist activity.

The compounds of formula I according to the present invention have a surprisingly high affinity for 5-$HT_6$ receptors. The high affinity of the compounds according to the invention for 5-$HT_6$ receptors is reflected in very low in-vitro receptor binding constants ($K_i$(5-$HT_6$) values) of as a rule less than 50 nM (nmol/l), preferably of less than 10 nM and, in particular of less than 5 nM. The displacement of $^3$H-LSD can, for example, be used in receptor binding studies for determining binding affinities to 5-$HT_6$ receptors.

Furthermore the compounds of formula I are highly selective 5-$HT_6$ receptor ligands which, because of their low affinity for other receptors such as dopamine receptors, adrenergic receptors, muscarinic receptors, histamine receptors, opiate receptors, in particular dopamine $D_2$, $_1$-adrenergic and histamine $H_1$ receptors, give rise to fewer side-effects than other, less selective 5-$HT_6$ ligands.

For instance the 5-$HT_6$/$D_2$, 5-$HT_6$/$_1$-adrenergic or 5-$HT_6$/$H_1$ selectivities of the compounds according to the present invention, i.e. the ratios $K_i$($D_2$)/$K_i$(5-$HT_6$), $K_i$($_1$-adrenergic)/

Commercially available nitroquinolines such as XII can be converted to the 3-iodo derivatives XIII by treatment with an iodinating reagent such as N-iodosuccinimide in a solvent such as acetic acid to yield the 3- or 4-iodoquinoline compound XIII. The 3- and 4-isomers can be separated at this stage or a later stage. Compound XIII is then reacted with an alkali metal salt of a sulfinic acid Ar—S(O)OH, e.g. the sodium salt Ar—S(O)$_2$Na, in the presence of a copper (I) salt such as Cu (I) triflate in a polar solvent such as N,N-dimethyl acetamide (DMA) or DMF. Reduction of the nitro group of XIV gives the amino compound XV. Reduction can be achieved by a variety methods, including reduction with "non-hydrogen" reducing agent such as SnCl$_2$ or by catalytic hydrogenation techniques familiar to those skilled in the art. The amino group of XV is then converted to the iodo group by a Sandmeyer reaction using a nitrosonium source (e.g. NaNO$_2$, n-BuNO$_2$) and a iodide (e.g. CuI or n-Bu$_4$NI) in a suitable solvent such water or CH$_3$CN.

Compounds of the formula IIIb,

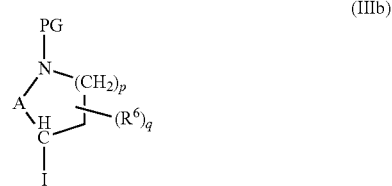

in particular compounds of the formula IIIb, wherein p is 0 and A is CH$_2$ can be prepared by the reaction sequence depicted in scheme 10.

$K_i$(5-HT$_6$) or $K_i$(H$_1$)/$K_i$(5-HT$_6$)) of the receptor binding constants, is as a rule at least 25, preferably at least 50, even better at least 100.

The displacement of [$^3$H]SCH23390 or [$^{125}$I]spiperone can be used, for example, for carrying out receptor binding studies on D$_1$, D$_2$ and D$_4$ receptors.

Furthermore the compounds of formula I because of their structural features are susceptible to display an enhanced brain penetration than other known 5-HT$_6$ receptor ligands.

Because of their binding profile, the compounds can be used for treating diseases which respond to 5-HT$_6$ receptor ligands (or which are susceptible to treatment with a 5-HT$_6$ receptor ligand), i.e. they are effective for treating those medical disorders or diseases in which exerting an influence on (modulating) the 5-HT$_6$ receptors leads to an improvement in the clinical picture or to the disease being cured. Examples of these diseases are disorders or diseases of the central nervous system.

Disorders or diseases of the central nervous system are understood as meaning disorders which affect the spinal cord and, in particular, the brain. Within the meaning of the invention, the term "disorder" denotes disturbances and/or anomalies which are as a rule regarded as being pathological conditions or functions and which can manifest themselves in the form of particular signs, symptoms and/or malfunctions. While the treatment according to the invention can be directed toward individual disorders, i.e. anomalies or pathological conditions, it is also possible for several anomalies, which may be causatively linked to each other, to be combined into patterns, i.e. syndromes, which can be treated in accordance with the invention.

The disorders which can be treated in accordance with the invention are in particular disorders which respond to a modulation of the 5-HT$_6$ receptor. They include cognitive dysfunctions, such as a deficit in memory, cognition and learning, in particular associated with Alzheimer's disease, age-related cognitive decline and mild cognitive impairment, attention deficit disorder/hyperactivity syndrome, personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowl Syndrome, diseases associated with neurodegeneration, such as stroke, spinal or head trauma and head injuries, such as hydrocephalus, drug addiction and obesity.

The addiction diseases include psychic disorders and behavioral disturbances which are caused by the abuse of psychotropic substances, such as pharmaceuticals or narcotics, and also other addiction diseases, such as addiction to gaming (impulse control disorders not elsewhere classified). Examples of addictive substances are: opioids (e.g. morphine, heroin and codeine), cocaine; nicotine; alcohol; substances which interact with the GABA chloride channel complex, sedatives, hypnotics and tranquilizers, for example benzodiazepines; LSD; cannabinoids; psychomotor stimulants, such as 3,4-methylenedioxy-N-methylamphetamine (ecstasy); amphetamine and amphetamine-like substances such as methylphenidate and other stimulants including caffeine. Addictive substances which come particularly into consideration are opioids, cocaine, amphetamine or amphetamine-like substances, nicotine and alcohol.

With regard to the treatment of addiction diseases, particular preference is given to those compounds according to the invention of the formula I which themselves do not possess any psychotropic effect. This can also be observed in a test using rats, which, after having been administered compounds which can be used in accordance with the invention, reduce their self administration of psychotropic substances, for example cocaine.

According to another aspect of the present invention, the compounds according to the invention are suitable for treating disorders whose causes can at least partially be attributed to an anomalous activity of 5-HT$_6$ receptors.

According to another aspect of the present invention, the treatment is directed, in particular, toward those disorders which can be influenced, within the sense of an expedient medicinal treatment, by the binding of preferably exogenously administered binding partners (ligands) to 5-HT$_6$ receptors.

The diseases which can be treated with the compounds according to the invention are frequently characterized by progressive development, i.e. the above-described conditions change over the course of time; as a rule, the severity increases and conditions may possibly merge into each other or other conditions may appear in addition to those which already exist.

The compounds of formula I can be used to treat a large number of signs, symptoms and/or malfunctions which are connected with the disorders of the central nervous system and, in particular, the abovementioned conditions. These signs, symptoms and/or malfunctions include, for example, a disturbed relationship to reality, lack of insight and ability to meet customary social norms or the demands made by life, changes in temperament, changes in individual drives, such as hunger, sleep, thirst, etc., and in mood, disturbances in the ability to observe and combine, changes in personality, in particular emotional lability, hallucinations, ego-disturbances, distractedness, ambivalence, autism, depersonalization and false perceptions, delusional ideas, chanting speech, lack of synkinesia, short-step gait, flexed posture of trunk and limbs, tremor, poverty of facial expression, monotonous speech, depressions, apathy, impeded spontaneity and decisiveness, impoverished association ability, anxiety, nervous agitation, stammering, social phobia, panic disturbances, withdrawal symptoms in association with dependency, maniform syndromes, states of excitation and confusion, dysphoria, dyskinetic syndromes and tic disorders, e.g. Huntington's chorea and Gilles-de-la-Tourette's syndrome, vertigo syndromes, e.g. peripheral positional, rotational and oscillatory vertigo, melancholia, hysteria, hypochondria and the like.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

The compounds according to the invention are preferentially suitable for treating diseases of the central nervous system, more preferably for treating cognitive dysfunctions and in particular, for treating cognitive dysfunctions associated with schizophrenia or with Alzheimer's disease.

According to another aspect of the invention the compounds of formula (I) are particularly suitable for treating addiction diseases caused for instance by the abuse of psychotropic substances, such as pharmaceuticals, narcotics, nicotine or alcohol, including psychic disorders and behavioral disturbances related thereto.

According to another aspect of the invention the compounds of formula (I) are particularly suitable for treating nutritional disorders, such as obesity, as well as diseases related thereto, such as cardiovascular diseases, digestive diseases, respiratory diseases, cancer or type 2 diabetes.

Within the context of the treatment, the use according to the invention of the described compounds involves a method. In this method, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.1 to 1000 mg/kg of bodyweight, in the case of oral administration, or of from about 0.1 to 100 mg/kg of bodyweight, in the case of parenteral administration, is supplied to an individual to be treated.

The invention also relates to the production of pharmaceutical compositions for treating an individual, preferably a mammal, in particular a human being, productive animal or domestic animal. Thus, the compounds of formula I are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more excipients. Excipients can be solid, semisolid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], $4^{th}$ edition, Aulendorf: ECV-Editio-Kantor-Verlag, 1996.

The following examples serve to explain the present invention without limiting its scope.

The compounds were either characterized via $^1$H-NMR in $d_6$-dimethylsulfoxid or d-chloroform on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts (δ) expressed in parts per million (ppm). The relative area of the shifts in the $^1$H-NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

PREPARATION EXAMPLES

I. Preparation of the Compounds

Example 1

8-(Azetidin-3-yl)-3-(phenylsulfonyl)quinoline hydrochloride 1.1 3-Hydroxy-azetidine-1-carboxylic acid tert-butyl ester To a degassed solution of 1-benzhydryl-azetidin-3-ol (4.75 g, 19.84 mmol) in methanol (MeOH) (150 ml) were added ammonium formate (8.76 g, 138.91 mmol), 10% Pd/C (450 mg) and Boc$_2$O (di-tert-butyl dicarbonate) (13 g, 59.56 mmol). The resulting suspension was heated to reflux under N$_2$ for 1 h. It was then cooled down to room temperature, filtered through a short pad of celite and concentrated. The residue was dissolved in CH$_2$Cl$_2$ and washed with water. The organic layer was dried over Na$_2$SO$_4$, filtered and concentrated in vacuo. Purification of the residue by flash column chromatography on silica gel (heptane:ethyl acetate (EtOAc), 1:1) afforded the title compound (3.30 g, 96%) as white crystals.

MS (ESI+): m/z=118.1 [M−tBu+H]$^+$; $^1$H-NMR (400 MHz, CDCl$_3$):=1.43 (s, 9H), 2.35 (d, J=6.2 Hz, 1H), 3.80 (dd, J=10.4, 4.4 Hz, 2H), 4.15 (dd, J=9.6, 6.7 Hz, 2H), 4.58 ppm (m, 1H).

1.2 3-Iodo-azetidine-1-carboxylic acid tert-butyl ester

A solution of 3-hydroxy-azetidine-1-carboxylic acid tert-butyl ester (3.35 g, 19.34 mmol) in toluene (200 ml) was treated with imidazole (3.95 g, 58.01 mmol), triphenyl-phosphine (10.14 g, 38.65 mmol) and I$_2$ (7.36 g, 28.99 mmol). The mixture was heated at 100° C. for 1 h, cooled down to room temperature and subsequently poured into a saturated aqueous solution of NaHCO$_3$ (30 ml). Excess triphenylphosphine was destroyed by addition of iodine until I$_2$ coloration persisted in organic layer. The latter was washed with an aqueous solution of Na$_2$S$_2$O$_3$ (5% strength), dried over Na$_2$SO$_4$, filtered and concentrated in vacuo. Purification of the residue by flash column chromatography (heptane:EtOAc, 2:1) provides the title compound (5.19 g, 95%) as a light yellow oil.

MS (ESI+): m/z=227.9 [M−tBu+H]$^+$; $^1$H-NMR (400 MHz, CDCl$_3$): =1.44 (s, 9H), 4.29 (dd, J=10.4, 5.4 Hz, 2H), 4.47 (m, 1H), 4.64 ppm (dd, J=9.5, 8.0 Hz, 2H).

1.3 (1-(tert-Butoxycarbonyl)azetidin-3-yl)zinc(II) iodide

Zn dust (1.80 g, 27.5 mmol) was vigorously stirred in DMA (11 ml) under nitrogen and the suspension was heated at 65° C. Trimethylsilyl chloride (0.37 g, 3.39 mmol) and 1,2-dibromoethane (0.64 g, 3.39 mmol) was added and stirring continued for 40 min. A solution of 3-iodo-azetidine-1-carboxylic acid tert-butyl ester (6.00 g, 21.2 mmol) in dimethylacetamide (DMA, 10 ml) was then added dropwise to the solution over a period of 30 min and then the reaction mixture allowed to cool to room temperature over 16 h. The resulting solution was used without any purification in the next step.

1.4 tert-Butyl 3-(3-(phenylsulfonyl)quinolin-8-yl)azetidine-1-carboxylate

To a solution of 8-iodo-3-(phenylsulfonyl)quinoline (200 mg, 0.51 mmol, prepared according to WO2003080580) in DMA (1 ml) was added PdCl$_2$(dppf) (8.3 mg, 0.10 mmol; dppf=1,1'-bis(diphenylphosphino)ferrocene) and CuI (11.6 mg, 0.06 mmol), followed by dropwise addition of (1-(tert-butoxycarbonyl)azetidin-3-yl)-zinc(II) iodide (317 mg, 0.91 mmol) in DMA (1 ml) over 10 min. The mixture was then heated at 80° C. for 6 h, then stirred at room temperature for 150 h and quenched with a saturated aqueous solution of NaCl. The reaction mixture was extracted with tert.-butylmethyl-ether (MTBE). The organic phases were dried over Na$_2$SO$_4$, filtered and concentrated in vacuo. The residue was purified by flash chromatography to give the title compound (54 mg, 25%) as a light yellow oil.

MS (ESI+): m/z=425.1 (M+H)$^+$, 370.1 (M−tBu+H)$^+$.

1.5 8-(Azetidin-3-yl)-3-(phenylsulfonyl)quinoline hydrochloride

A solution of tert-butyl 3-(3-(phenylsulfonyl)quinolin-8-yl)azetidine-1-carboxylate (54 mg, 0.13 mmol) in CH$_2$Cl$_2$ (3 ml) was treated with hydrochloric acid (1M in ether, 0.3 ml) at 0° C. and then stirred at room temperature for 16 h. After concentration, the product was washed with EtOAc and dried in vacuo to give the title compound (45 mg, 98%) as a white solid.

MS (ESI+): m/z=325.1 (M+H)$^+$; $^1$H-NMR (400 MHz, d$_6$-DMSO): =3.32 (m, 1H), 3.47 (m, 1H), 4.58 (m, 1H), 5.38 (m, 1H), 5.47 (m, 1H), 7.72 (m, 2H), 7.80 (m, 1H), 8.16 (m, 3H), 8.42 (m, 2H), 8.73 (s, 3H), 9.92 (s, 1H), 10.38 ppm (s, 1H).

Example 2

3-(Phenylsulfonyl)-8-(piperidin-4-yl)quinoline hydrochloride

The title compound was prepared in an analogous manner to that described for preparation example 1.

2.1 tert-Butyl 4-(3-(phenylsulfonyl)quinolin-8-yl)piperidine-1-carboxylate

Yield: 45%; MS (ESI+): m/z=453.1 (M+H)$^+$, 397.1 (M−tBu+H)$^+$.

2.2 3-(Phenylsulfonyl)-8-(piperidin-4-yl)quinoline hydrochloride

Yield: 62%; MS (ESI+): m/z=353.1 (M+H)$^+$; $^1$H-NMR (400 MHz, DMSO): =2.00 (m, 4H), 3.09 (m, 2H), 4.58 (m, 1H), 5.38 (m, 1H), 5.47 (m, 1H), 7.72 (m, 2H), 7.80 (m, 1H), 8.16 (m, 3H), 8.42 (m, 2H), 8.73 (s, 3H), 9.92 (s, 1H), 10.38 ppm (s, 1H).

Example 3

8-(1-Benzylpyrrolidin-3-yl)-3-(phenylsulfonyl)quinoline 3-(Phenylsulfonyl)-8-vinylquinoline (210 mg, 0.71 mmol, prepared according to WO2007039219) was reacted with benzyl methoxymethyl trimethylsilylmethyl amine (253 mg, 1.07 mmol) in dichloromethane (2 ml) in the presence of trifluoroacetic acid for 20 minutes. The solution was washed with a saturated aqueous solution of NaHCO$_3$ solution, dried over MgSO$_4$, filtered and concentrated in vacuo. The residue was purified by chromatography (100% dichloromethane) to give the title compound as a colourless oil (100 mg, 33%).

MS (ESI+): m/z=429.1 (M+H)$^+$; $^1$H-NMR (400 MHz, d$_6$-DMSO): =2.22 (m, 1H), 3.00 (m, 1H), 3.22 (m, 1H), 3.35 (m, 1H), 3.60 (m, 1H), 3.75 (m, 2H), 4.00 (m, 1H), 5.26 (d, 1H), 5.72 (d, 1H), 7.11 (m, 2H), 7.32 (m, 11H), 7.50 (m, 1H), 7.68 (d, 2H), 7.77 ppm (s, 1H).

Example 4

8-(Piperidin-4-yl)-3-(3-(trifluoromethyl)phenylsulfonyl)quinoline

The title compound was prepared in an analogous manner to that described for preparation example 1.

4.1 tert-Butyl 4-(3-(3-(trifluoromethyl)phenylsulfonyl)quinolin-8-yl)piperidine-1-carboxylate Yield: 26%; $^1$H-NMR (400 MHz, d$_6$-DMSO): =1.43 (s, 9H), 1.60 (m, 2H), 1.82 (m, 2H), 2.90 (m, 2H), 4.10 (m, 3H), 7.81 (m, 2H), 5.47 (m, 1H), 7.92 (m, 1H), 8.19 (m, 2H), 8.47 (m, 3H), 8.67 (br m, 1H), 9.30 (s, 1H), 9.43 ppm (s, 1H).

4.2 8-(Piperidin-4-yl)-3-(3-(trifluoromethyl)phenylsulfonyl)quinoline

Yield: 98%; MS (ESI+): m/z=421.1 (M+H)$^+$; $^1$H-NMR (400 MHz, d$_6$-DMSO):=2.00 (m, 4H), 3.17 (m, 2H), 4.20 (m, 1H), 7.81 (m, 2H), 5.47 (m, 1H), 7.92 (m, 1H), 8.19 (m, 2H), 8.47 (m, 3H), 8.67 (br m, 1H), 9.30 (s, 1H), 9.43 ppm (s, 1H).

Example 5

3-(4-Fluorophenylsulfonyl)-8-(piperidin-4-yl)quinoline

The title compound was prepared in an analogous manner to that described for preparation example 1.

5.1 tert-Butyl 4-(3-(4-fluorophenylsulfonyl)quinolin-8-yl)piperidine-1-carboxylate Yield: 41%; MS (ESI+): m/z=415.1 (M+H−tBu)$^+$; $^1$H-NMR (400 MHz, d$_6$-DMSO): =1.42 (s, 9H), 1.67 (m, 2H), 1.82 (m, 2H), 2.90 (m, 2H), 4.10 (m, 3H), 7.49 (m, 2H), 7.73 (m, 1H), 7.86 (m, 1H), 8.15 (m, 3H), 9.15 (s, 1H), 9.36 ppm (s, 1H).

5.2 3-(4-Fluorophenylsulfonyl)-8-(piperidin-4-yl)quinoline

Yield: 96%; MS (ESI+): m/z=371.1 (M+H)$^+$; $^1$H-NMR (400 MHz, d$_6$-DMSO):=2.02 (m, 4H), 3.10 (m, 2H), 3.39 (m, 2H), 4.16 (m, 1H), 7.49 (m, 2H), 7.79 (m, 2H), 8.16 (m, 3H), 9.15 (s, 1H), 9.34 ppm (s, 1H).

Example 6

3-(3-Bromophenylsulfonyl)-8-(piperidin-4-yl)quinoline

The title compound was prepared in an analogous manner to that described for preparation example 1.

6.1 3-(3-Bromophenylsulfonyl)-8-iodoquinoline

MS (ESI+): m/z=473.8, 475.8 (M+H)$^+$; $^1$H-NMR (400 MHz, d$_6$-DMSO): =7.59 (m, 2H), 7.95 (d, 1H), 8.12 (d, 1H), 8.30 (d, 1H), 8.62 (d, 1H), 9.35 (s, 1H), 9.48 ppm (s, 1H).

6.2 tert-Butyl 4-(3-(3-bromophenylsulfonyl)quinolin-8-yl)piperidine-1-carboxylate Yield: 54%; MS (ESI+): m/z=475.0, 477.0 (M+H−tBu)$^+$; $^1$H-NMR (400 MHz, d$_6$-DMSO): =1.48 (s, 9H), 1.67 (m, 2H), 1.82 (m, 2H), 2.90 (m, 2H), 4.10 (m, 3H), 7.62 (t, 2H), 7.73 (t, 1H), 7.86 (d, 1H), 7.89 (d, 1H), 8.13 (m, 3H), 8.30 (s, 1H), 9.18 (s, 1H), 9.38 ppm (s, 1H).

6.3 3-(3-Bromophenylsulfonyl)-8-(piperidin-4-yl)quinoline

Yield: 91%; MS (ESI+): m/z=431.0, 433.0 (M+H)$^+$; $^1$H-NMR (400 MHz, d$_6$-DMSO):=2.02 (m, 4H), 3.10 (m, 2H), 3.39 (m, 2H), 4.16 (m, 1H), 7.60 (t, 1H), 7.79 (m, 2H), 7.90 (m, 1H), 8.14 (m, 2H), 8.30 (s, 1H), 9.25 (s, 1H), 9.39 ppm (s, 1H).

Example 7

8-(Piperidin-4-yl)-3-(3-(pyrrolidin-1-yl)phenylsulfonyl)quinoline

7.1 tert-Butyl-4-(3-(3-(pyrrolidin-1-yl)phenylsulfonyl)quinolin-8-yl)piperidine-1-carboxylate A solution of tert-butyl 4-(3-(3-bromophenylsulfonyl) quinolin-8-yl)piperidine-1-carboxylate (100 mg, 0.19 mmol), pyrrolidine (40 mg, 0.564 mmol), Na tert.-butanolate (32 mg, 0.34 mmol), tris(dibenzylideneacetone)dipalladium (0) chloroform adduct (19 mg, 0.019 mmol) and [1,1'-binaphthalene]-2,2'-diylbis(diphenylphosphine) (BINAP, 23 mg, 0.038 mmol) in 10 mL tetrahydrofurane (THF) was heated at reflux for 2 hours. The cooled solution, after standard aqueous workup and chromatography, yielded 60 mg (61%) of the BOC-protected product as a yellow solid.

MS (ESI+): m/z=422.3 (M+H−tBu)$^+$; $^1$H-NMR (400 MHz, d$_6$-DMSO): =0.87 (d, 1H), 1.28 (m, 2H), 1.48 (s, 9H), 1.63 (m, 2H), 1.82 (m, 2H), 1.98 (m, 4H), 2.90 (m, 2H), 4.10 (m, 3H), 6.70 (m, 2H), 7.07 (s, 1H), 7.20 (d, 1H), 7.38 (m, !H), 7.73 (m, 1H), 7.84 (d, 1H), 8.13 (m, 1H), 9.18 (s, 1H), 9.38 ppm (s, 1H).

7.2 8-(Piperidin-4-yl)-3-(3-(pyrrolidin-1-yl)phenylsulfonyl)quinoline

The title compound was prepared in an analogous manner to that described for preparation example 1.

Yield: 88%; MS (ESI+): m/z=431.0 (M+H)$^+$; $^1$H-NMR (400 MHz, DMSO):=2.02 (m, 8H), 3.16 (m, 2H), 3.27 (m, 4H), 3.40 (m, 2H), 4.22 (m, 1H), 6.80 (d, 1H), 7.09 (s, 2H), 7.22 (d, 1H), 7.40 (m, 1H), 7.80 (m, 2H), 8.14 (m, 12H), 8.30 (s, 1H), 9.15 (s, 1H), 9.35 ppm (s, 1H).

II. Biological Investigations

Displacement of Radioligands Binding to the Following Cloned Human Receptors

1. Preparation of Membranes by Ultrasonic Treatment and Differential Centrifugation Cells from stable clonal cell lines expressing the corresponding receptor (5-HT$_6$, $_1$-adrenergic, dopamine D$_2$ or histamine H$_1$ receptors) were washed with PBS (w/o Ca$^{++}$, Mg$^{++}$) and harvested in PBS with 0.02% EDTA. The cells were collected by centrifugation at 500 g for 10 min. at 4° C., washed with PBS and centrifuged (500 g, 10 min. 4° C.). The pellets were stored at −80° C. until use. For membrane preparation, the thawed cell pellet was resuspended in ice-cold sucrose buffer (0.25 M sucrose, 10 mM Hepes (pH 7.4), 1 mM Phenylmethylsulfonyl fluoride (PMSF) in DMSO, 5 g/ml Pepstatin-A, 3 mM EDTA, 0.025% Bacitracin) and homogenized with a Branson Sonifier W-250 (Settings: Timer 4; Output Control 3; Duty Cycle constant; 2 to 3 cycles). Cell disruption was checked with the aid of a microscope. Remaining unbroken cells were pelleted at 1,000 g for 10 min. at 4° C. The sucrose buffer supernatant was then centrifuged at 60,000 g for 1 h at 4° C. (Beckman Ultrazentrifuge XL 80). The pellet was resuspended in 30 ml ice-cold Tris buffer (20 mM TRIS (pH 7.4), 5 g/ml Pepstatin A, 0.1 mM PMSF, 3 mM EDTA) by pipetting through a 10 ml serological pipet and centrifuged for 1 h at 4° C. at 60,000 g. A final resuspension was performed in a small volume of ice-cold Tris buffer (see above) by pressing through a serological pipet followed by ultrasonic treatment with a Branson Sonifier W-250 (Settings: Timer 1; Output Control 3; Duty Cycle constant; 1 cycle). Protein concentration was determined (BCA-Kit; Pierce) and aliquots stored at −80° C. or in liquid nitrogen for long-term storage.

2. Receptor Binding Experiments

All receptor binding experiments were carried out in the corresponding assay buffer in a total volume of 200 μl in the presence of various concentrations of test compound (10$^{-5}$ M to 10$^{-9}$ M, tenfold serial dilution, duplicate determinations). The assays were terminated by filtration on polyethylenimine (PEI 0.1% or 0.3%) presoaked Packard Unifilter Plates (GF/C or GF/B) with a Tomtec MachIII U 96 well-plate harvester. After the plates had been dried for 2 h at 55° C. in a drying chamber scintillation cocktail (BetaPlate Scint; PerkinElmer) was added. Radioactivity was measured in a Microbeta Trilux two hours after the addition of the scintillation mixture. Data derived from liquid scintillation counting were analysed by iterative non-linear regression analysis with the use of the Statistical Analysis System (SAS): a program similar to "LIGAND" as described by Munson and Rodbard (Analytical Biochemistry 107, 220-239 (1980)).

a) 5-HT$_6$ Receptor Binding Assay

HEK293 cells stably expressing the h-5-HT$_6$ receptor (NCBI Reference Sequence XM 001435) were cultured in RPMI1640 medium supplemented with 25 mM HEPES, 10% fetal calf serum and 1-2 mM glutamine. The membrane preparation was performed as described in section 1. For these membranes a $K_D$ of 1.95 nM for [$^3$H]-LSD (Lysergic Acid Diethylamide; Amersham, TRK1038) was determined by means of saturation binding experiments. On the day of the assay, the membranes were thawed, diluted in assay buffer (50 mM Tris-HCl, 5 mM CaCl$_2$, 0.1% ascorbic acid, 10 μM pargyline, pH 7.4) to a concentration of 8 μg protein/assay and homogenized by gentle vortexing For inhibition studies, 1 nM [$^3$H]-Lysergic Acid Diethylamide was incubated in the presence of various concentrations of test compound in assay buffer. Non-specific binding was defined with 1 μM methiothepin. The binding reaction was carried out for 3.5 h at room temperature. During the incubation, the plates were shaken on a plate shaker at 100 rpm and terminated by filtration on Packard Unifilter GF/C (0.1% PEI) plates, followed by 2 wash cycles with ice-cold 50 mM Tris-HCl, 5 mM CaCl$_2$.

a) Dopamine D$_2$ Receptor Binding Assay

HEK293 cells stably expressing the dopamine D$_2$ receptor (NCBI Reference Sequence NM_000795) were cultured in RPMI1640 medium supplemented with 25 mM HEPES, 10% fetal calf serum and 1-2 mM glutamine. The membrane preparation was performed as described in section 1. For these membranes a $K_D$ of 0.22 nM for [$^{125}$I]-iodospiperone (PerkinElmer Life Sciences, NEX284) was determined by means of saturation binding experiments. On the day of the assay, the membranes were thawed, diluted in assay buffer (50 mM Tris-HCl, 120 mM NaCl, 5 mM MgCl$_2$, 5 mM KCl, 1.5 mM CaCl$_2$, pH 7.4) to a concentration of 15 μg protein/assay and homogenized by gentle vortexing. For inhibition studies, 0.01 nM [$^{125}$I]-iodospiperone (PerkinElmer Life Sciences, NEX284) was incubated in the presence of various concentrations of test compound in assay buffer. Non-specific binding was defined with 1 μM haloperidol. The binding reaction was carried out for 1 h at room temperature and terminated by filtration on Packard Unifilter GF/B (0.1% PEI) plates, followed by 6 wash cycles with an ice-cold 7% polyethyleneglycol solution.

b) $_1$-Adrenergic Receptor Binding Assay

CHO-K$_1$ cells stably expressing the $_1$-adrenergic receptor (NCBI Reference Sequence NM_033303) were cultured in RPMI1640 medium supplemented with 25 mM HEPES, 10% fetal calf serum and 1-2 mM glutamine. The membrane preparation was performed as described in section 1. For these membranes a $K_D$ of 0.12 nM for [$^3$H]-prazosine (PerkinElmer Life Sciences, NET823) was determined by means of saturation binding experiments. On the day of the assay, the membranes were thawed, diluted in assay buffer (50 mM Tris-HCl, pH 7.4) to a concentration of 4 μg protein/assay and homogenized by gentle vortexing. For inhibition studies, 0.1 nM [$^3$H]-prazosine (PerkinElmer Life Sciences, NET823) was incubated in the presence of various concentrations of test compound in assay buffer. Non-specific binding was defined with 1 μM phentolamine. The binding reaction was carried out for 1 h at room temperature and terminated by filtration on Packard Unifilter GF/C (0.1% PEI) plates, followed by 3 wash cycles with ice-cold assay buffer.

c) H$_1$ Receptor Binding Assay

CHO-K$_1$ cells stably expressing the histamine H$_1$ receptor (Euroscreen-ES-390-C, NCBI Reference Sequence NM_000861) were cultured in RPMI1640 medium supplemented with 25 mM HEPES, 10% fetal calf serum and 1-2 mM glutamine. The membrane preparation was performed as described in section 1. For these membranes a $K_D$ of 0.83 nM for [$^3$H]-pyrilamine (PerkinElmer Life Sciences, NET594) was determined by means of saturation binding experiments. On the day of the assay, the membranes were thawed, diluted in assay buffer (50 mM Na$_2$HPO$_4$, 50 mM KH$_2$PO$_4$, pH 7.4) to a concentration of 6 μg protein/assay and homogenized by gentle vortexing. For inhibition studies, 1 nM [$^3$H]-pyrilamine (PerkinElmer Life Sciences, NET594) was incubated in the presence of various concentrations of test compound in assay buffer. Non-specific binding was defined with 1 μM pyrilamine. The binding reaction was carried out for 50 minutes at room temperature and terminated by filtration on Packard Unifilter GF/C (0.3% PEI) plates, followed by 2 wash cycles with ice-cold assay buffer.

3. Data Analysis

Data derived from liquid scintillation counting were analyzed by iterative non-linear regression analysis with the use of the Statistical Analysis System (SAS): a program similar to "LIGAND" as described by Munson and Rodbard (Anal. Biochem. 1980, 107, 220-239). Fitting was performed according to formulae described by Feldman (Anal. Biochem. 1972, 48, 317-338). IC$_{50}$, nH and K$_i$ values were expressed as geometrical mean. For receptors with a low affinity for the test compound, where the highest tested compound concentration inhibited less than 30% of specific radioligand binding, K$_i$-values were determined according to the equation of Cheng and Prusoff (Biochem. Pharmacol. 1973, 22, 2099-2108) and expressed as greater than (>).

The results of the receptor binding studies are expressed as receptor binding constants $K_i$(5-HT$_6$), $K_i$(D$_2$), $K_i$($_1$-adrenergic) and $K_i$(H$_1$), respectively, as described herein before, and given in table I.

In these tests, the compounds according to the invention exhibit very good affinities for the 5-HT$_6$ receptor ($K_i$<250 nM or <50 nM or <20 nM and frequently <1 nM). Furthermore those compounds bind selectively to the 5-HT$_6$ receptor, as compared to the affinity for the D$_2$, the $_1$-adrenergic or the H$_1$ receptors. These compounds exhibit little affinities for the D$_2$, $_1$-adrenergic or H$_1$ receptors ($K_i$>250 nM or >1000 nM and frequently >10000 nM).

The results of the receptor binding studies on the human 5-HT6 receptor are compiled in table B. In table B (+) in each case indicates a $K_i$-value of >1 M, (++) in each case indicates a $K_i$-value of 100 nM-1 M and (+++) in each case indicates a $K_i$-value of <100 nM.

TABLE B

| Example | Ki (human 5-HT6) |
|---------|------------------|
| 1 | +++ |
| 2 | +++ |
| 3 | + |
| 4 | +++ |
| 5 | +++ |
| 6 | +++ |
| 7 | +++ |

We claim:
1. Quinoline compounds of formula (I)

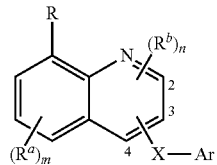

wherein
R is a moiety of the formulae

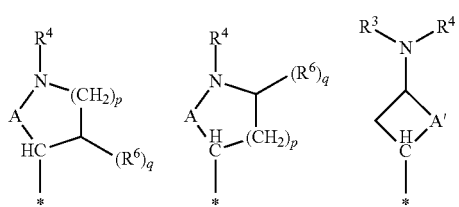

wherein
* indicates the binding site to the quinolinyl radical;
A is a chemical bond, $CHR^5$ or $CH_2CHR^5$;
A' is a single bond, $CH_2$, $CH_2CH_2$, $CHR^7$ or $CH_2CHR^7$;
$R^3$ is hydrogen or $C_1$-$C_4$-alkyl;
$R^4$ is hydrogen, $C_1$-$C_6$-alkyl, $C_1$-$C_6$-hydroxyalkyl, $C_1$-$C_6$-haloalkyl, $C_1$-$C_6$-alkoxy-$C_1$-$C_4$-alkyl, $C_1$-$C_6$-haloalkoxy-$C_1$-$C_4$-alkyl, $C_3$-$C_6$-cycloalkyl, $C_3$-$C_6$-halocycloalkyl, $C_3$-$C_6$-cycloalkyl-$C_1$-$C_4$-alkyl, aryl-$C_1$-$C_4$-alkyl, hetaryl-$C_1$-$C_4$-alkyl, $C_3$-$C_6$-alkenyl, $C_3$-$C_6$-haloalkenyl, formyl, $C_1$-$C_4$-alkylcarbonyl or $C_1$-$C_4$-alkoxycarbonyl;
$R^5$ is hydrogen, $C_1$-$C_4$-alkyl, $C_1$-$C_4$-haloalkyl, $C_1$-$C_4$-alkoxy or $C_1$-$C_4$-haloalkoxy;
$R^6$ is $C_1$-$C_4$-alkyl, $C_1$-$C_4$-haloalkyl, $C_1$-$C_4$-alkoxy or $C_1$-$C_4$-haloalkoxy; or
$R^5$ and $R^6$ together may also be linear $C_1$-$C_4$-alkylene, which may carry 1 or 2 radicals $R^9$;
$R^7$ and $R^9$ are independently selected from the group consisting of $C_1$-$C_4$-alkyl, $C_1$-$C_4$-haloalkyl, $C_1$-$C_4$-alkoxy and $C_1$-$C_4$-haloalkoxy;
n is 0, 1 or 2;
m is 0, 1, 2 or 3;
p is 0, 1, 2 or 3;
q is 0 or 1;
$R^a$, $R^b$ are independently selected from the group consisting of halogen, CN, $C_1$-$C_4$-alkyl, $C_1$-$C_4$-haloalkyl, $C_1$-$C_4$-alkoxy, $C_1$-$C_4$-haloalkoxy, $C(O)R^{aa}$, $C(O)NR^{cc}R^{bb}$ and $NR^{cc}R^{bb}$; wherein $R^{aa}$ is hydrogen, $C_1$-$C_4$-alkyl, $C_1$-$C_4$-haloalkyl, $C_1$-$C_4$-alkoxy or $C_1$-$C_4$-haloalkoxy, and $R^{cc}$, $R^{bb}$ are independently selected from the group consisting of hydrogen and $C_1$-$C_4$-alkyl;
X is $CH_2$, $C(O)$, S, $S(O)$ or $S(O)_2$; which is located in the 3- or 4-position of the quinoline ring;
Ar is a radical $Ar^1$, $Ar^2$—$Ar^3$ or $Ar^2$—O—$Ar^3$, wherein $Ar^1$, $Ar^2$ and $Ar^3$ are each independently selected from the group consisting of aryl or hetaryl wherein aryl or hetaryl moieties may be unsubstituted or may carry 1, 2, 3 substituents $R^x$, wherein
$R^x$ is halogen, CN, $NO_2$, $C_1$-$C_6$-alkyl, $C_1$-$C_6$-haloalkyl, $C_1$-$C_6$-hydroxyalkyl, $C_1$-$C_6$-alkoxy-$C_1$-$C_4$-alkyl, $C_2$-$C_6$-alkenyl, $C_2$-$C_6$-haloalkenyl, $C_3$-$C_6$-cycloalkyl, $C_3$-$C_6$-halocycloalkyl, $C_1$-$C_6$-alkoxy, $C_1$-$C_6$-hydroxyalkoxy, $C_1$-$C_6$-alkoxy-$C_1$-$C_4$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_6$-alkylcarbonyl, $C_1$-$C_6$-haloalkylcarbonyl, $C_1$-$C_6$-alkylcarbonylamino, $C_1$-$C_6$-haloalkylcarbonylamino, carboxy, NH—C(O)—$NR^{x1}R^{x2}$, $NR^{x1}R^{x2}$, $NR^{x1}R^{x2}$—$C_1$-$C_6$-alkylene, O—$NR^{x1}R^{x2}$, wherein $R^{x1}$ and $R^{x2}$ in the last 4 mentioned radicals are independently of each other hydrogen, $C_1$-$C_6$-alkyl, $C_1$-$C_6$-haloalkyl or $C_1$-$C_6$-alkoxy or $R^{x1}$ and $R^{x2}$ in the last 4 mentioned radicals together with the nitrogen atom form an N-bound 5-, 6- or 7-membered, saturated heterocycle which is unsubstituted or which carries 1, 2, 3 or 4 radicals selected from $C_1$-$C_4$-alkyl, $C_1$-$C_4$-haloalkyl, $C_1$-$C_4$-hydroxyalkyl and $C_1$-$C_4$-alkoxy and wherein 2 radicals $R^x$, which are bound to adjacent carbon atoms of Ar may form a saturated or unsaturated 5- or 6-membered carbocyclic or heterocyclic ring, which itself may carry a radical Rx;
and physiologically tolerated acid addition salts and the N-oxides thereof.

2. The compounds as claimed in claim 1, wherein the moiety R is a radical of the formulae:

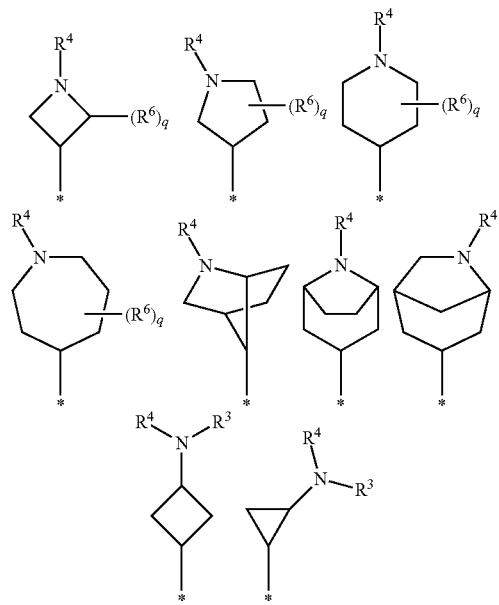

wherein $R^3$, $R^4$ and $R^6$ are as defined in claim 1, * indicates the binding site to the quinolinyl radical and wherein q is 0 or 1.

3. The compounds as claimed in claim 1, wherein the moiety R is a radical of the formulae:

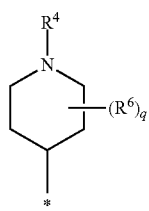

wherein $R^4$ and $R^6$ are as defined in claim 1, * indicates the binding site to the quinolinyl radical and wherein q is 0 or 1.

4. The compounds as claimed in claim 1, wherein $R^4$ is hydrogen.

5. The compounds as claimed in claim 1, wherein X is $SO_2$.

6. The compounds as claimed in claim 1, wherein X is $CH_2$.

7. The compounds as claimed in claim 1, wherein X is C(O).

8. The compounds as claimed in claim 1, wherein X is located in the 3-position of the quinolinyl moiety.

9. The compounds as claimed in claim 1, wherein X is located in the 4-position of the quinolinyl moiety.

10. The compounds as claimed in claim 1, wherein Ar is phenyl, naphthyl, thienyl, pyridyl, pyrimidyl, pyrazolyl, imidazolyl, oxazolyl, isoxazolyl, thiazolyl, triazolyl, thiadiazolyl, quinolinyl, isoquinolinyl, tetrahydroisoquinolinyl, benzofuranyl, benzothienyl, benzoxazinyl, benzothiazolyl, benzoxadiazolyl, benzothiadiazolyl, benzomorpholinyl or indanyl, wherein the cyclic radical Ar is unsubstituted or may carry 1, 2 or 3 substituents $R^x$ as defined in claim 1.

11. The compounds as claimed in claim 10, wherein Ar is phenyl, which is unsubstituted or may carry 1, 2 or 3 substituents $R^x$ as defined in claim 1.

12. The compounds as claimed in claim 1, wherein Rx is selected from halogen, CN, $C_1$-$C_4$-alkyl, $C_1$-$C_4$-haloalkyl, $C_1$-$C_4$alkoxy, $C_1$-$C_4$-haloalkoxy, $C_3$-$C_6$-cycloalkyl and a group $NR^{x1}R^{x2}$.

13. The compounds as claimed in claim 1, wherein m is 0.

14. The compounds as claimed in claim 1, wherein n is 0.

15. A pharmaceutical composition comprising at least one compound as claimed in claim 1, optionally together with at least one physiologically acceptable carrier or auxiliary substance.

16. A method for treating a medical disorder selected from diseases of the central nervous system, addiction diseases or obesity, said method comprising administering an effective amount of at least one compound as claimed in claim 1 to a subject in need thereof.

17. The method as claimed in claim 16, wherein the medical disorder is a disease of the central nervous system.

18. The method as claimed in claim 16, for treating cognitive dysfunctions.

19. The method as claimed in claim 16, for treating cognitive dysfunctions associated with Alzheimer's disease.

20. The method as claimed in claim 16, for treating cognitive dysfunctions associated with schizophrenia.

21. The method as claimed in claim 16, wherein the medical disorder is an addiction disease.

22. The method as claimed in claim 16, wherein the medical disorder is obesity.

23. A method for treating a medical disorder selected from diseases of the central nervous system, addiction diseases or obesity, the method comprising administering to a patient in need of treatment thereof a pharmaceutical composition as claimed in claim 15.

* * * * *